US009600625B2

(12) United States Patent
Asadi et al.

(10) Patent No.: US 9,600,625 B2
(45) Date of Patent: Mar. 21, 2017

(54) SYSTEMS AND METHODS FOR PROCESSING NUCLEIC ACID SEQUENCE DATA

(71) Applicant: Bina Technologies, Inc., Redwood City, CA (US)

(72) Inventors: Narges Bani Asadi, Redwood City, CA (US); Jike Chong, Sunnyvale, CA (US); Henry Chen, Cupertino, CA (US); Marghoob Mohiyuddin, Foster City, CA (US); Austin Doupnik, Redwood City, CA (US)

(73) Assignee: BINA TECHNOLOGIES, INC., Redwood City, CA (US)

( * ) Notice: Subject to any disclaimer, the term of this patent is extended or adjusted under 35 U.S.C. 154(b) by 711 days.

(21) Appl. No.: 13/868,985

(22) Filed: Apr. 23, 2013

(65) Prior Publication Data
US 2013/0338934 A1 Dec. 19, 2013

Related U.S. Application Data

(60) Provisional application No. 61/637,247, filed on Apr. 23, 2012, provisional application No. 61/722,755, filed on Nov. 5, 2012, provisional application No. 61/722,768, filed on Nov. 5, 2012.

(51) Int. Cl.
*G06F 19/00* (2011.01)
*G06F 19/22* (2011.01)

(52) U.S. Cl.
CPC .................................. *G06F 19/22* (2013.01)

(58) Field of Classification Search
CPC .......... G06F 19/22; G06F 19/18; G06F 19/24; G06F 17/30424; G06F 17/30554; G06F 19/28; G06F 19/10; G06F 19/20; G06F 19/26; G06F 17/18; G06F 17/30321; G06F 17/30371; G06F 17/30595; G06F 19/16
See application file for complete search history.

(56) References Cited

U.S. PATENT DOCUMENTS

| | | | |
|---|---|---|---|
| 5,873,052 | A | 2/1999 | Sharaf |
| 6,741,986 | B2 | 5/2004 | Cho et al. |
| 6,772,160 | B2 | 8/2004 | Cho et al. |
| 7,363,346 | B2 | 4/2008 | Groner et al. |
| 7,379,959 | B2 | 5/2008 | Hinni et al. |
| 7,577,683 | B2 | 8/2009 | Cho et al. |
| 7,640,256 | B2 | 12/2009 | Inglis |
| 7,650,339 | B2 | 1/2010 | Cho et al. |
| 8,060,552 | B2 | 11/2011 | Hinni et al. |
| 8,165,978 | B1 | 4/2012 | Batra |
| 8,200,746 | B2 | 6/2012 | Hinni et al. |
| 8,209,130 | B1 | 6/2012 | Kennedy et al. |
| 2006/0036368 | A1 | 2/2006 | Chen et al. |
| 2007/0162411 | A1 | 7/2007 | Kupershmidt et al. |
| 2008/0033819 | A1 | 2/2008 | Leschly |
| 2009/0049019 | A1 | 2/2009 | Su et al. |
| 2009/0222400 | A1 | 9/2009 | Kupershmidt et al. |
| 2010/0010957 | A1 | 1/2010 | Cho et al. |
| 2010/0049445 | A1 | 2/2010 | Fofanov et al. |
| 2010/0057374 | A1 | 3/2010 | Wong et al. |
| 2010/0057807 | A1 | 3/2010 | Wong et al. |
| 2010/0121872 | A1 | 5/2010 | Subramaniam |
| 2010/0153017 | A1 | 6/2010 | De La Vega et al. |
| 2010/0161237 | A1 | 6/2010 | Pratt et al. |
| 2010/0169026 | A1 | 7/2010 | Sorenson et al. |
| 2010/0198774 | A1 | 8/2010 | Fasulo |
| 2010/0287165 | A1 | 11/2010 | Halpern et al. |
| 2010/0318528 | A1 | 12/2010 | Kupershmidt et al. |
| 2011/0004413 | A1 | 1/2011 | Carnevali et al. |
| 2011/0060974 | A1 | 3/2011 | Viger et al. |
| 2011/0202280 | A1 | 8/2011 | Sikora et al. |
| 2011/0231277 | A1 | 9/2011 | Campbell |
| 2011/0252420 | A1 | 10/2011 | Tung et al. |
| 2011/0257889 | A1 | 10/2011 | Klammer et al. |
| 2011/0264377 | A1 | 10/2011 | Cleary |
| 2011/0270533 | A1 | 11/2011 | Zhang et al. |
| 2011/0295514 | A1 | 12/2011 | Breu et al. |

(Continued)

FOREIGN PATENT DOCUMENTS

| | | | |
|---|---|---|---|
| WO | WO 2011/145955 A1 | 11/2011 | |
| WO | WO 2012/034030 A1 | 3/2012 | |
| WO | WO 2012/039633 A1 | 3/2012 | |

OTHER PUBLICATIONS

Langmead, B. et al. Searching for SNP's with Cloud Computing. 2009 Genome Biology vol. 10: R134.*
Schatz, M. C. CloudBurst: highly sensitive read mapping with MapReduce, 2009, Bioinformatics vol. 25 No. 11 p. 1363-1369.*
Zhang et al Nucleic Acids Research (published online Feb. 2012) vol. 40 No. 11 p. e83.*
Chen et al. Nucleic Acids Research (published online Dec. 2011) vol. 40 No. 6 e42.*
Li. A statistical framework for SNP calling, mutation discovery, association mapping and population genetical parameter estimation from sequencing data. Bioinformatics Nov. 1, 2011;27(21):2987-93. doi: 10.1093/bioinformatics/btr509. Epub Sep. 8, 2011.

(Continued)

*Primary Examiner* — Mary Zeman
(74) *Attorney, Agent, or Firm* — Kilpatrick, Townsend & Stockton LLP

(57) ABSTRACT

The present disclosure provides systems and methods for nucleic acid sequence analysis. A system for processing raw nucleic acid sequence data from a genomic sequencer comprises a data processing server having a housing contained therein one or more processing modules. The one or more processing modules can each comprise an electronic control unit programmed to align nucleic acid sequence data from a genomic sequencing device and perform one or more of variant analysis and structural variant analysis on the nucleic acid sequence data. The system can further comprise a computer server in communication with the processing server. The computer server can be programmed or otherwise configured to process and/or analyze the aligned nucleic acid sequence data.

23 Claims, 30 Drawing Sheets

(56) References Cited

U.S. PATENT DOCUMENTS

| | | |
|---|---|---|
| 2012/0011086 A1 | 1/2012 | Zhang et al. |
| 2012/0046877 A1 | 2/2012 | Hyland et al. |
| 2012/0053845 A1 | 3/2012 | Bruestle et al. |
| 2012/0072581 A1 | 3/2012 | Tung et al. |
| 2012/0078901 A1 | 3/2012 | Conde |
| 2012/0089338 A1 | 4/2012 | Roth |
| 2012/0095697 A1 | 4/2012 | Halpern et al. |
| 2012/0102041 A1 | 4/2012 | Park et al. |
| 2012/0102054 A1 | 4/2012 | Popescu et al. |
| 2012/0110013 A1 | 5/2012 | Conde et al. |
| 2012/0183953 A1 | 7/2012 | Xiao et al. |
| 2012/0191366 A1 | 7/2012 | Pearson et al. |
| 2012/0197533 A1 | 8/2012 | Nazarenko et al. |
| 2012/0197623 A1 | 8/2012 | Homer |
| 2012/0209792 A1 | 8/2012 | Grossman |
| 2013/0311106 A1* | 11/2013 | White .................. G06F 19/20 702/20 |

OTHER PUBLICATIONS

Mu, et al. Fast and accurate read alignment for resequencing. Bioinformatics. Sep. 15, 2012;28(18):2366-73. doi: 10.1093/bioinformatics/bts450. Epub Jul. 18, 2012.

Needleman, et al. A general method applicable to the search for similarities in the amino acid sequence of two proteins. J Mol Biol. Mar. 1970;48(3):443-53.

Rognes. Faster Smith-Waterman database searches with inter-sequence SIMD parallelisation. BMC Bioinformatics. Jun. 1, 2011;12:221. doi: 10.1186/1471-2105-12-221.

Smith, et al. Identification of common molecular subsequences. J Mol Biol. Mar. 25, 1981;147(1):195-7.

Langmead, Ben, et al., "Searching for SNPs with cloud computing," Genome Biology, 2009, 10:R134-134.10.

Wang, Jun, et al., "The diploid genome sequence of an Asian individual," Nature, 2008, 456:60-65.

Bias, Randy, "Amazon's EC2 Generating 220M+ Annually," 2009, available at http://cloudscaling.com/blog/cloud-computing/amazons-ec2-generatng-220m-annually/.

Li, Heng and Durbin, Richard, "Fast and accurate short read alignment with Burrows-Wheeler transform," Bioinformatics, 2009, 25, 14:1754-1760.

De Bona, Fabio, et. al., "Optimal spliced alignments of short sequence reads," Bioinformatics, 2008, 24, 16:i174-i180.

Rudy, Gabe, "A Hitchhiker's Guide to Next Generation Sequencing—Part 2," 2010, available at http://blog.goldenhelix.com/grudy/a-hitchhiker's-guide-to-next-generation-sequencing-Part-2/.

* cited by examiner

SYSTEMS AND METHODS FOR PROCESSING NUCLEIC ACID SEQUENCE DATA

CROSS-REFERENCE

This application claims priority to U.S. Provisional Patent Application No. 61/637,247, filed Apr. 23, 2012, U.S. Provisional Patent Application No. 61/722,755 filed Nov. 5, 2012, and U.S. Provisional Patent Application No. 61/722,768, filed Nov. 5, 2012, which are entirely incorporated herein by reference.

BACKGROUND

Advances in next-generation sequencing technologies have enabled faster and cheaper generation of whole genome sequencing data, and opened new possibilities for the use of whole genome data for research, clinical, and personalized medicine applications. With a greater number of genomes being sequenced, new challenges have arisen in the storage and analysis of whole genome data, which can comprise several terabytes (TB). It has been estimated that the cost of storing genomic sequence data will soon outstrip the cost of sequencing the genome. The size of these large datasets presents challenges in the physical storage of data, the memory, power, and time requirements for processing and analyzing the data, and the transfer of data to, for instance, a cloud server.

In order to unlock the full potential of whole genome sequencing, there is a need for technologies that make the storage, processing, and analysis of data more manageable and cost-effective.

SUMMARY

This disclosure provides an integrated hardware and software platform for processing and analyzing raw nucleic acid sequence data. In some embodiments, raw nucleic acid sequence data is processed (e.g., alignment, variant analysis, structural variant (or variation) analysis) on a server comprising one or more modules. The processed data is subsequently directed to a remote server that provides access to a user and, in some cases, enables subsequent analysis (e.g., variant analysis, structural variant analysis).

An aspect of the present disclosure provides a system for processing genetic sequence data from a genomic sequencing device comprising a programmable logic device that is programmed to perform alignment, variant analysis and structural variant analysis on the genetic sequence data with at least about thirty times coverage in a time period less than or equal to about 4 hours. In one embodiment, the time period is less than or equal to about 3 hours. In another embodiment, the time period is less than or equal to about 1 hour. In some cases, the system further comprises a memory location with machine-executable code that upon execution by the programmable logic device implements a method, the method comprising aligning the genetic sequence data to provide aligned genetic sequence data, and performing variant analysis and/or structural variant analysis on the aligned genetic sequence data. In one embodiment, the programmable logic device is programmed to perform alignment on the genetic sequence data with at least about 95% accuracy as measured by a percentage of mapped reads. In another embodiment, the programmable logic device is programmed to perform at least about 200,000 alignments per second on the genetic sequence data with at least about 95% accuracy as measured by a percentage of mapped reads.

Another aspect of the present disclosure provides a system for processing genetic sequence data from a genomic sequencing device, comprising a field programmable gate array that is programmed to perform alignment on the genetic sequence data with at least about 95% accuracy as measured by a percentage of mapped reads. In one example, the field programmable gate array is programmed to perform at least about 200,000 alignments per second on the genetic sequence data with at least about 96% accuracy. In another embodiment, the field programmable gate array is programmed to perform at least about 200,000 alignments per second on the genetic sequence data with at least about 97% accuracy. In another embodiment, the field programmable gate array is programmed to perform at least about 200,000 alignments per second on the genetic sequence data with at least about 98% accuracy. In another embodiment, the field programmable gate array is programmed to perform at least about 200,000 alignments per second on the genetic sequence data with at least about 99% accuracy. In some cases, the field programmable gate array is programmed to perform between about 200,000 and 12 million alignments per second. In one embodiment, the field programmable gate array is programmed to perform at least about 1 million alignments per second. In another embodiment, the field programmable gate array is programmed to perform at least about 10 million alignments per second. In another embodiment, the field programmable gate array is programmed to perform at least about 12 million alignments per second.

Another aspect of the present disclosure provides a system comprising an electronic control unit that is programmed to perform at least about 200,000 alignments per second on genetic sequence data with at least about 95% accuracy as measured by a percentage of mapped reads. In one embodiment, the electronic control unit is programmed to perform at least about 200,000 alignments per second on the genetic sequence data with at least about 96% accuracy. In another embodiment, the electronic control unit is programmed to perform at least about 200,000 alignments per second on the genetic sequence data with at least about 97% accuracy. In another embodiment, the electronic control unit is programmed to perform at least about 200,000 alignments per second on the genetic sequence data with at least about 98% accuracy. In another embodiment, the electronic control unit is programmed to perform at least about 200,000 alignments per second on genetic sequence data with at least about 99% accuracy. In some cases, the electronic control unit is programmed to perform between about 200,000 and 12 million alignments per second. In one example, the system is programmed to perform at least about 1 million alignments per second. In another example, the system is programmed to perform at least about 10 million alignments per second. In another example, the system is programmed to perform at least about 12 million alignments per second. In one embodiment, the system is programmed to perform at least about 1 billion alignments per hour. In one case, the electronic control unit is a programmable logic device. In some cases, the electronic control unit is a field programmable gate array.

Another aspect of the present disclosure provides a system comprising a server comprising an electronic control unit that is programmed to perform alignment, variant analysis and structural variant analysis on genetic sequence data from a genomic sequencing device with at least about thirty times coverage of the genetic data in a time period less than or equal to about 4 hours. In one embodiment, the time period is less than or equal to about 3 hours. In another embodiment, the time period is less than or equal to about 1 hour. In some cases, the electronic control unit comprises a computer processor. In an embodiment, the electronic control unit comprises a field-programmable gate array. In another embodiment, the server further comprises an aligner module in communication with a data server, wherein the aligner module is programmed to align the genetic sequence data from the genomic sequencing device, and wherein the data server is programmed to direct the genetic sequence data to the aligner module. In one embodiment, the aligner module is in communication with the electronic control unit. In another embodiment, the system further comprises an in-memory genome region sorter that is programmed to sort genetic sequence data.

Another aspect of the present disclosure provides a system for processing raw genetic sequence data from a genomic sequencer, comprising: (a) a data processing server having a housing contained therein one or more processing modules, the one or more processing modules each having an electronic control unit comprising a processor programmed to (i) align raw genetic sequence data from a genomic sequencing device to provide aligned genetic sequence data and (ii) perform one or more of variant analysis and structural variant analysis on the aligned genetic sequence data, wherein the data processing server performs alignment and one or more of variant analysis and structural variant analysis in at least about thirty times coverage in a time period less than or equal to about 4 hours; and (b) a computer server in network communication with the processing server, the computer server programmed to process and/or analyze the aligned genetic sequence data. In one embodiment, the system further comprises a genomic sequencer in communication with the data processing server, wherein the genomic sequencer generates the raw genetic sequence data. In another embodiment, an individual module comprises at least one aligner cell that is configured to align the genetic sequence data. In some cases, the system further comprises a display in communication with the computer server, wherein the display is configured to present, on a user interface, the results of an analysis of the aligned genetic sequence data. In one embodiment, the data processing server is programmed to perform at least about 200,000 alignments per second on the raw genetic sequence data with at least about 96% accuracy.

Another aspect of the present disclosure provides a method for generating genetic sequence information, comprising performing, with the aid of a server comprising an electronic control unit, alignment and variant analysis and/or structural variant analysis on genetic sequence data from a genomic sequencing device with at least about thirty times coverage of the genetic sequence data in a time period less than or equal to about 4 hours. In one embodiment, the time period is less than or equal to about 3 hours. In another embodiment, the time period is less than or equal to about 1 hour. In some cases, the electronic control unit performs alignment on the genetic sequence data with at least about 95% accuracy as measured by a percentage of mapped reads. In one embodiment, the electronic control unit performs at least about 200,000 alignments per second on the genetic sequence data with at least about 95% accuracy as measured by a percentage of mapped reads. In some cases, the electronic control unit is programmed with a trained algorithm for performing alignment of the genetic sequence data. In one embodiment, the electronic control unit comprises a multi core processor and performing the alignment comprises (i) distributing the alignment of individual subsets of the genetic sequence data to individual cores of the multi core processor, and (ii) performing alignment of the individual subsets of the genetic sequence data at substantially the same time. In another embodiment, the method further comprises distributing the alignment of the individual subsets of the genetic sequence data together with one or more reference sequences to the individual cores of the multi core processor. In another embodiment, the server further comprises a memory location, and the alignment further comprises packaging reference sequences in the memory location and generating vectorization ordering from the reference sequences, and aligning the genetic sequence data with the aid of the reference sequences. In some cases, the alignment further comprises generating read sequence data and the read sequence data is repackaged to match the vectorization ordering of the reference sequences. In some cases, the genetic sequence data comprises a plurality of individual nucleic acid sequence data from the genomic sequencing device.

Another aspect of the present disclosure provides a method for processing raw genetic sequence data from a genomic sequencer, comprising: (a) retrieving raw genetic sequence data corresponding to at least a portion of the genomic sequence of a subject generated by a genetic sequencing device and (b) processing the raw genetic sequence data with the aid of a data processing server having a housing contained therein one or more processing modules, the one or more processing modules each having an electronic control unit comprising a processor programmed to: (i) align raw genetic sequence data corresponding to the genomic sequence of a subject to provide aligned genetic sequence data, and (ii) perform one or more of variant analysis and structural variant analysis on the aligned genetic sequence data, thereby providing processed genetic sequence data, wherein (i) and (ii) performed with at least about thirty times coverage in a time period less than or equal to about 4 hours. The method further comprises (c) directing the processed genetic sequence data to a computer server in network communication with the processing server, the computer server programmed to analyze the processed genetic sequence data. In some cases, the time period is less than or equal to about 3 hours. In some cases, the time period is less than or equal to about 1 hour. In an embodiment, the electronic control unit performs alignment on the genetic sequence data with at least about 95% accuracy as measured by a percentage of mapped reads. In another embodiment, the electronic control unit performs at least about 200,000 alignments per second on the genetic sequence data with at least about 95% accuracy as measured by a percentage of mapped reads. In some cases, the electronic control unit is programmed with a trained algorithm for performing alignment of the genetic sequence data.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings or figures (also "FIG." or "FIGs." herein) of which:

DETAILED DESCRIPTION

Figure 1:
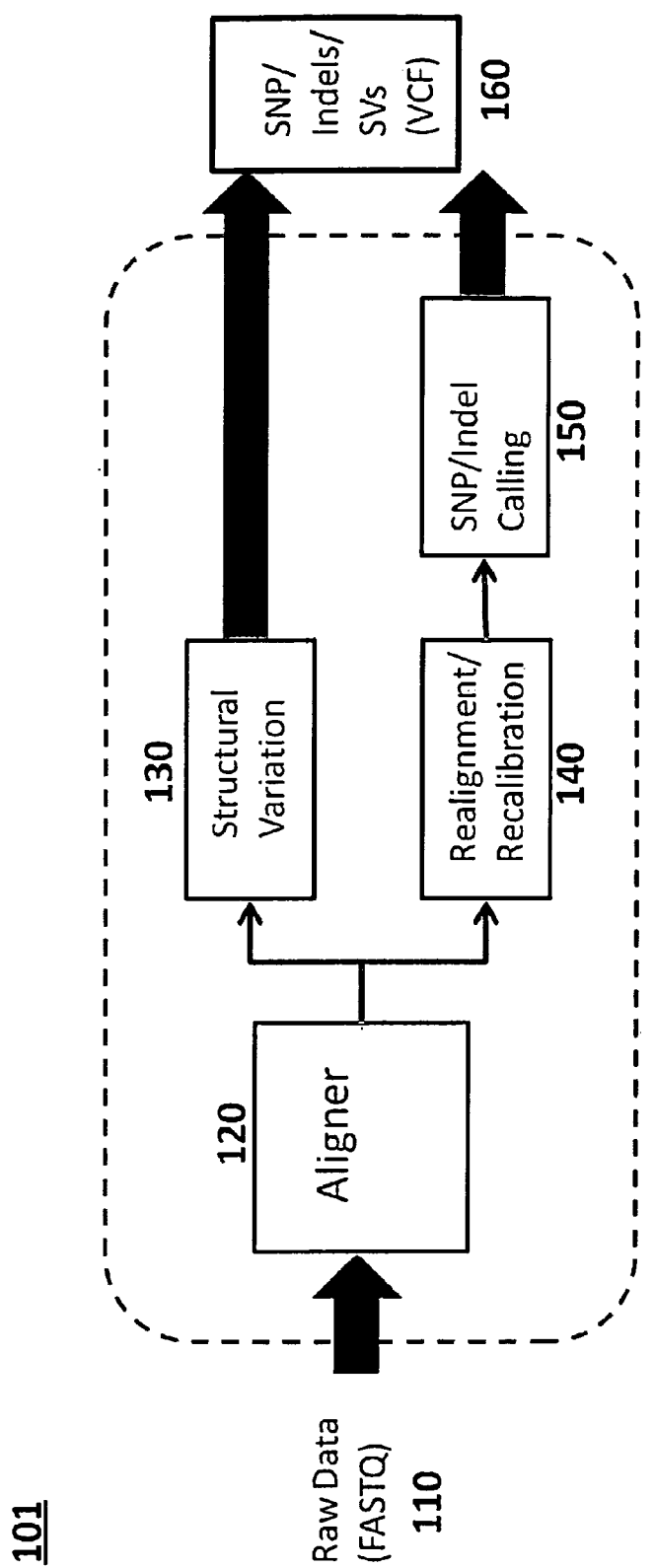
FIG. 1 illustrates a workflow for sequence alignment and variant analysis, in accordance with an embodiment of the invention.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed in practicing the invention.

The term "sequencing" generally refers to methods and technologies for determining the sequence of nucleotide bases in one or more polynucleotides. The polynucleotides can be, for example, deoxyribonucleic acid (DNA) or ribonucleic acid (RNA), including variants or derivatives thereof (e.g., single stranded DNA).

The term "genome" generally refers to an entirety of an organism's hereditary information. A genome can be encoded either in DNA or in RNA. A genome can comprise regions that code for proteins as well as non-coding regions. A genome can include the sequence of all chromosomes together in an organism. For example, the human genome has a total of 46 chromosomes. The sequence of all of these together constitutes the human genome.

The term "read" generally refers to a sequence of sufficient length (e.g., at least about 30 base pairs (bp)) that can be used to identify a larger sequence or region, e.g., that can be aligned to a location on a chromosome or genomic region or gene.

The term "coverage" generally refers to the average number of reads representing a given nucleotide in a reconstructed sequence. It can be calculated from the length of the original genome (G), the number of reads (N), and the average read length (L) as N*L/G. For instance, sequence coverage of 30× means that each base in the sequence has been read 30 times.

The term "alignment" generally refers to the arrangement of sequence reads to reconstruct a longer region of the genome. Reads can be used to reconstruct chromosomal regions, whole chromosomes, or the whole genome.

The terms "variant" or "polymorphism" and generally refers to one of two or more divergent forms of a chromosomal locus that differ in nucleotide sequence or have variable numbers of repeated nucleotide units. Each divergent sequence is termed an allele, and can be part of a gene or located within an intergenic or non-genic sequence. The most common allelic form in a selected population can be referred to as the wild-type or reference form. Examples of variants include, but are not limited to single nucleotide polymorphisms (SNPs) including tandem SNPs, small-scale multi-base deletions or insertions, also referred to as indels or deletion insertion polymorphisms or DIPs), Multi-Nucleotide Polymorphisms (MNPs), Short Tandem Repeats (STRs), deletions, including microdeletions, insertions, including microinsertions, structural variations, including duplications, inversions, translocations, multiplications, complex multi-site variants, copy number variations (CNV). Genomic sequences can comprise combinations of variants. For example, genomic sequences can encompass the combination of one or more SNPs and one or more CNVs.

The term "single nucleotide polymorphism" (SNP) generally refers to a single base (nucleotide) polymorphism in a DNA sequence among individuals in a population. A SNP may be present within coding sequences of genes, non-coding regions of genes, or in the intergenic regions between genes. SNPs within a coding sequence may not necessarily change the amino acid sequence of the protein that is produced, due to degeneracy of the genetic code. A SNP which results in a different polypeptide sequence compared to that produced by a reference or wild-type allele is referred to as "nonsynonymous". A nonsynonymous change can either be missense or "nonsense", where a missense change results in a different amino acid, while a nonsense change results in a premature stop codon. In some cases, a SNP can also arise from a deletion of a nucleotide or an insertion of a nucleotide relative to a reference or wild-type allele.

The term "indel" generally refers to a class of mutations that include nucleotide insertions, deletions, or combinations thereof. In coding regions of the genome, an indel may cause a frameshift mutation, unless the length of the indel is a multiple of 3. Frameshift mutations can cause significant changes in the coding of amino acids that make up a polypeptide, often rendering the polypeptide nonfunctional. Frameshift mutations caused by indels can result in severe genetic disorders, e.g., Tay-Sachs Disease.

The term "structural variant" generally refers to a variation in structure of an organism's chromosome greater than 1 kb in length. Structural variants can comprise many kinds of variation in the genome, and can include, for example, deletions, duplications, copy-number variants, insertions, inversions and translocations, or chromosomal abnormalities. Typically a structure variation affects a sequence length about 1 Kb to 3 Mb, which is larger than SNPs and smaller than chromosome abnormality. In some cases, structural variants are associated with genetic diseases.

The term "calling" generally refers to identification. For example, "base calling" means identification of bases in a polynucleotide sequence, "SNP calling" generally means the identification of SNPs in a polynucleotide sequence, "variant calling" means the identification of variants in a genomic sequence.

The term "raw genetic sequence data" generally refers to unaligned genetic sequencing data, such as from a genetic sequencing device. In an example, raw genetic sequence data following alignment yields genetic information that can be characteristic of the whole or a coherent portion of genetic information of a subject for which the raw genetic sequence data was generated. Genetic sequence data can include a sequence of nucleotides, such as adenine (A), guanine (G), thymine (T), cytosine (C) and/or uracil (U). Genetic sequence data can include one or more nucleic acid sequences. In some cases, genetic sequence data includes a plurality of nucleic acid sequences, at least some of which can overlap. For example, a first nucleic acid sequence can be (5' to 3') AATGGGC and a second nucleic acid sequence can be (5' to 3') GGCTTGT. Genetic sequence data can have various lengths and nucleic acid compositions, such as from one nucleic acid in length to at least 5, 10, 20, 30, 40, 50, 100, 1000, 10,000, 100,000, or 1,000,000 base pairs (double or single stranded) in length.

Systems and methods provided herein can be used with genetic data, such as deoxyribonucleic acid (DNA) or ribonucleic acid (RNA) data. Such genetic data can be provided by a genetic sequencing device, such as, with limitation, an Illumina, Pacific Biosciences, Oxford Nanopore, or Life Technologies (Ion Torrent) sequencing device. Such devices may provide a plurality of raw genetic data corresponding to the genetic information of a subject (e.g., human), as generated by the device from a sample provided by the subject. In some situations, systems and methods provided herein may be used with proteomic information.

Computational Platforms

In an aspect, the disclosure provides computational, integrated hardware/software platforms and tools for whole genome and targeted sequencing data analysis. In some cases, a platform can also be used for analysis of RNASeq and ChipSeq data. In some embodiments, the platform is optimized for executing methods such as compression, processing, and analysis of raw data generated from various sequencers, such as, e.g., HiSeq, MiSeq, Genome Analyzer, SOLID, 454, Ion Torrent, and Pacific Biosciences. One of skill in the art will understand that the current invention can be used not only for genomic data, but can be utilized for the compression, processing, and analysis of any dataset.

An example workflow (101) is depicted in FIG. 1, illustrating the execution of several methods by a platform described herein. As shown in FIG. 1, raw data (110) is aligned using one or more alignment algorithms (120). For example, an alignment algorithm may include the SeqAlto algorithm (see e.g., Mu et al., BIOINFORMATICS, 2012; 28(18):2366-73, which is entirely incorporated herein by reference). The aligned sequence data is then processed in parallel by one or more structural variation algorithms (130) and one or more realignment/recalibration algorithms (140). Realigned and recalibrated sequence data is further processed by one or more SNP/indel calling algorithms (150). The output (160) of the platform includes information on SNPs, insertions, deletions, and/or structural variants of the aligned sequence data.

Alignment of Raw Data

An aspect of the disclosure provides methods for rapidly aligning raw reads with high fidelity. Such raw reads may correspond to raw genetic sequence data. Such methods may include the incorporation of one or more alignment algorithms and can be optimized to align reads of specific lengths, or may process reads outside of their optimized lengths with lesser fidelity and speed. Furthermore, a platform described herein may offer users the ability to trade alignment accuracy for efficiency. In other cases, a platform may target high-quality reads with a low number of gaps as errors.

Alignment algorithms that may be utilized by a platform may take a genome hashing approach and use either or both of large contiguous seeds and adaptive stopping techniques. Adaptive stopping techniques may be used to declare each read to be aligned based on the current best alignment and the number of seeds examined. The combination of a genome hashing approach and either or both of these techniques may improve alignment efficiency when compared to other methods and may also allow the platform to make use of longer reads. The use of longer reads may improve the alignment of reads with larger indels, without a loss in alignment sensitivity, when the targeted read lengths are greater than about 100 bp.

The use of large contiguous seeds may require large amounts of memory to store an index. To minimize the use of memory, an alignment platform, for example, may use a sub-sampling approach to fit an entire genome into less than or equal to about 8 GB of memory.

In some cases, alignment algorithms may comprise a string comparison algorithm. In such an algorithm, the number of mismatches between corresponding elements of two strings of the same length are compared. For example, a sequence read may be compared with a reference read. The algorithm continues along the strings until either all elements of the strings have been compared (alignment is achieved, or when a threshold algorithm score (such as, for example, the number of "mismatches"—i.e., differences between the two strings) is achieved signifying that the alignment is unacceptable.

Alignment of reads may consist of multiple phases. In some cases, a single-ended alignment phase (comprising a ungapped alignment algorithm and, if ungapped alignment fails, a gapped alignment algorithm) is followed by a pairing stage. During the pairing stage, if a discordant result is obtained, an ungapped alignment may be followed by a gapped alignment to find a concordant alignment.

String comparison algorithms may be called when ungapped alignment is desired. One goal of a string comparison algorithm may be to find alignments with no gaps and small numbers of mismatches. In general, a string comparison has a time-dependence on the read length of the compared strings.

Alignment algorithms may comprise a Needleman-Wunsch algorithm (see e.g., Needleman and Wunsch, J. MOL. BIO. 1970; 48(3):443-453, which is entirely incorporated herein by reference). In general, a Needleman-Wunsch algorithm performs a global alignment of two strings (such as, for example, a sequence read and a reference read) using dynamic programming to compute an optimum score. In some cases, the algorithm constructs a scoring matrix of size nxm (n corresponding to the length of the first string and n corresponding to the length of the second string) and an optimum score occurs in the last row of the matrix. As with string comparison, there may be an early stopping criterion which terminates the algorithm when a threshold value alignment score gets higher than a certain threshold, indicating that the alignment is unacceptable. In some cases, one of two variations of the Needleman-Wunsch algorithm may be used. In the first case, only an optimum score is computed. In the second case, an optimum score and a corresponding backtrace are computed. The backtrace is a sequence of edits (insertions, deletions, matches, mismatches) which can transform a reference read to the read for the optimum score.

A Needleman-Wunsch algorithm may be called when gapped alignment is desired. In general, the Needleman-Wunsch algorithm has a time dependence on the lengths of both strings under comparison.

Alignment algorithms may comprise a Smith-Waterman algorithm (see, e.g., Smith and Waterman, J. MOL. BIO. 1981; 25(1): 195-197, which is entirely incorporated herein by reference). The Smith-Waterman algorithm is similar to the Needleman-Wunsch algorithm in that it uses dynamic programming to align two strings, but also differs as the algorithm performs local alignments rather than global. Moreover, unlike the Needleman-Wunsch algorithm, the early stopping criterion using a threshold score may be omitted in cases where the optimal score can be anywhere in the scoring matrix. Similar to the Needleman-Wunsch algorithm, the Smith-Waterman algorithm, one of two variations of the algorithm may be used—computing only an optimum score or computing both an optimum score and a corresponding backtrace.

A Smith-Waterman algorithm may be called when gapped alignment is desired, including for a pairing stage. In general, the Smith-Waterman algorithm has a time dependence on the length of both strings under comparison.

Moreover, the Needleman-Wunsch and Smith-Waterman algorithms may be used to detect rare variants and large insertion and deletions in a genome.

Variant and Structural Variant Analysis

Another aspect of the present disclosure provides integrated platforms that can reliably and accurately call sequence variants, such as single nucleotide polymorphisms (SNPs), indels, and structural variants after sequence reads have been aligned. In some embodiments, methods described herein feature highly optimized variant calling pipelines capable of quickly calling SNPs, insertions, and deletions in a read alignment.

Platforms described herein may include variant analysis tools. Non-limiting examples of algorithms or tools that may be used for variant calling include the Broad Institute's Genome Analysis Toolkit (GATK) and Samtools mpileup (see e.g., Li, BIOINFORMATICS, 2011; 27(1):2987-2993, which is entirely incorporated herein by reference). In some cases, a platform described herein may enhance the utility of such variant analysis tools, in that greater time efficiency in variant calling may be achieved without sacrificing the accuracy of the appropriate variant calling tool.

In some embodiments, a platform may include methods developed for structural variant calling. In one example method, the sequenced genome is divided into non-overlapping windows. The method takes as an input the number of reads centered within each window, which it can debias by taking into account the mappability and GC content. The method can then estimate the mean for each window, using a penalty which forces neighboring windows to have similar values. In some cases, this may make the read counts smoother, and may help to avoid false positives when the raw read count vector is analyzed. After estimating the mean for every bin, windows that show an anomalous read count can be tagged as variation regions. In some embodiments, the method proceeds by merging those regions and estimating the breakpoints of the duplications/deletions. The copy number can be estimated by averaging the raw values within a detected region.

Hardware and Hardware/Software Integration

Platforms described herein generally provide hardware for retrieving, processing and analyzing genomic data. Hardware can be programmed/integrated with various algorithms (e.g., machine learning algorithms) and other software packages, including those described herein, to execute sequence read alignment methods, variant analysis methods, structural variant analysis methods, statistical analysis methods, or any other appropriate method.

Figure 8:
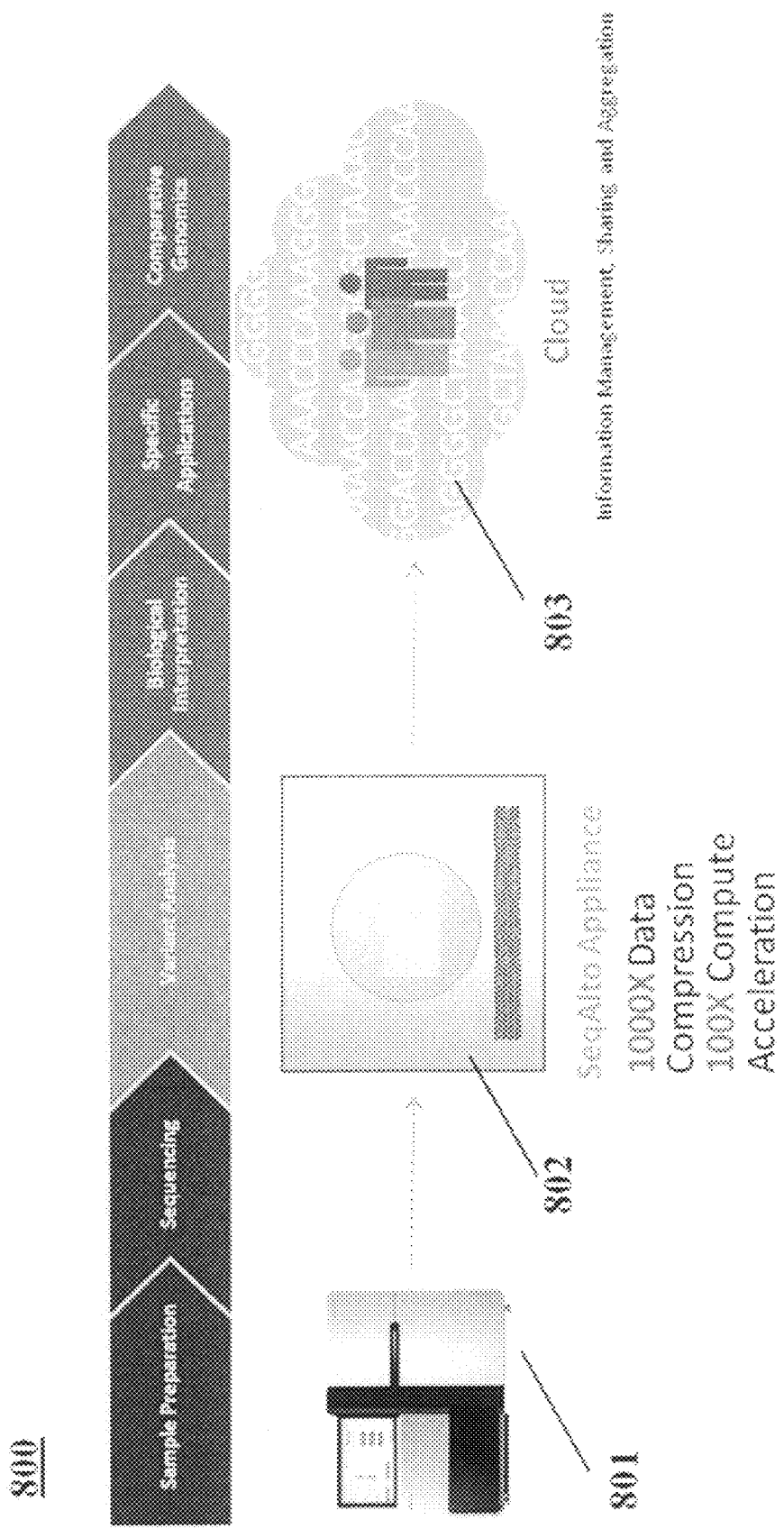
FIG. 8 shows a workflow, in accordance with an embodiment of the invention.

FIG. 8 shows an exemplary workflow 800, in accordance with an embodiment of the invention. A sample is sequenced by a genomic sequencer 801 to provide raw sequence information. A hardware/software platform (802) processes the information, such as by performing alignment of raw data and subsequent variant analysis. The platform can include a server or plurality of servers. The platform may compress the raw data from the sequencer by a factor of at least about 1000, and processes the sample at a rate that is increased (or accelerated) by a factor of at least about 100 in relation to other system currently available. Processed data is subsequently stored in a remote computer system (803) which provides information management, sharing and aggregation. The processed information on the cloud can be analyzed by the platform or a remote computer system In some embodiments, an integrated hardware/software platform comprises a device or sub-system for interface with a gene sequencer. In some embodiments, the platform design is optimized to interface with a specific sequencer, such as an Illumina sequencer or Ion Torrent sequencer.

In some embodiments, an integrated hardware/software platform comprises one or more CPUs that are 8 bit or 16-bit, such as in a single instruction, multiple data (SIMD) configuration. Such hardware can perform operations on multiple data in parallel.

In some embodiments, an integrated hardware/software platform comprises one or more graphics processing units (GPU's). A graphics processing unit (GPU) is a specialized electronic circuit that can manipulate and alter memory in a way that accelerates the building of images in a frame buffer that outputs to a display. In some embodiments, the platform is GPU achieved. In some embodiments, the platform is GPU-bound.

In some embodiments, an integrated hardware/software platform comprises one or more field programmable gate arrays (FPGAs). The terms "field programmable gate array" or "FPGA" generally refer to a circuit that can be configured by the customer or designer after manufacturing. In some embodiments, the FPGA configuration is specified using a hardware description language (HDL). In some embodiments, the platform is FPGA achieved. In an embodiment, the platform is FPGA bound, which may improve alignment scoring speed.

Figure 11:
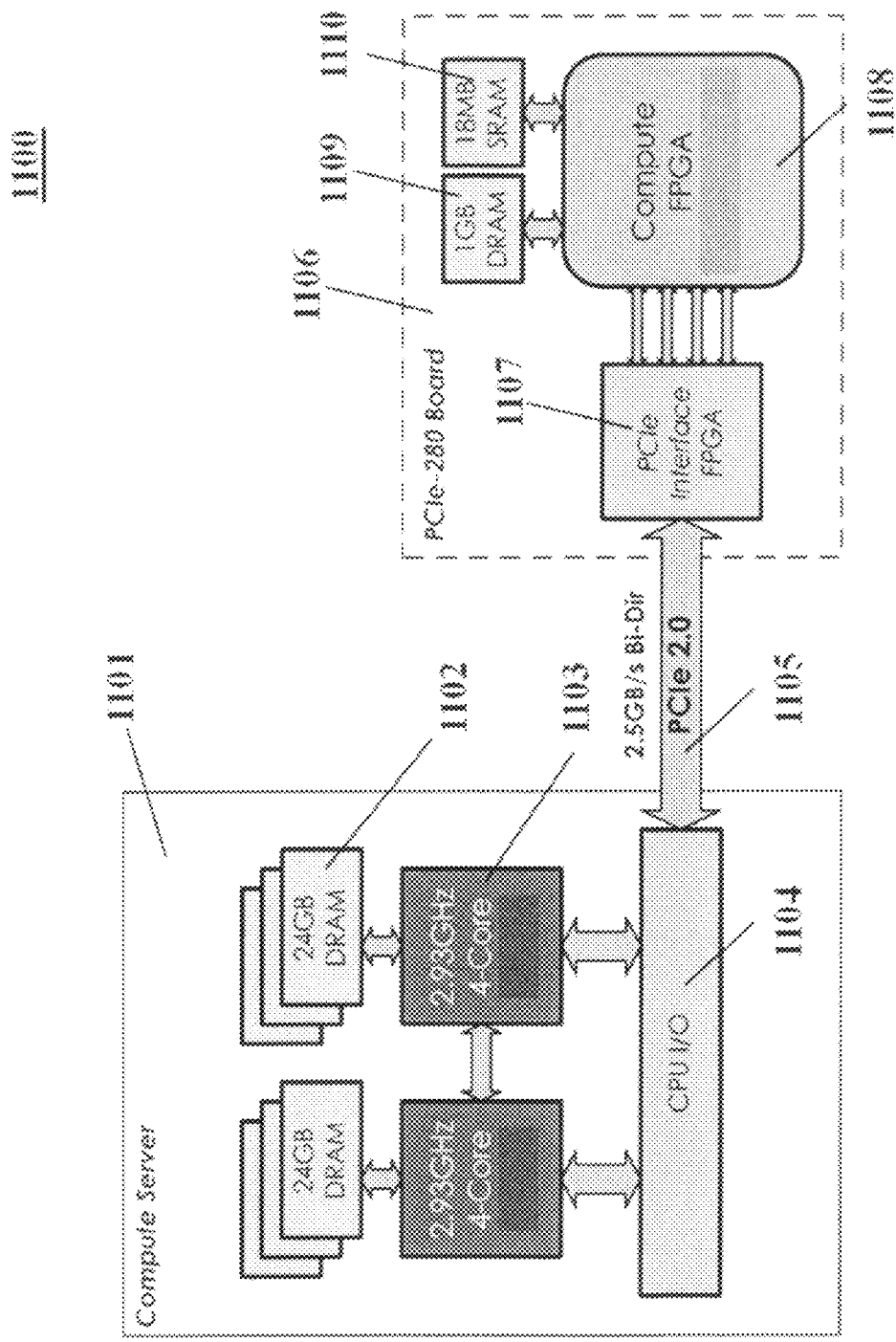
FIGS. 11-15 show various computer platforms, in accordance with some embodiments of the invention.

FIG. 11 shows an example hardware configuration 1100, in accordance with an embodiment of the invention. The configuration comprises a computer server 1101 comprising dynamic random access memory (1101—DRAM) coupled to one or more processors (1103 e.g., two 4-core processors in the illustrated example). The DRAM and processors are in communication with an input/output interface (1104). A communications bus (1105) couples the CPU I/O to a PCIe-280 board (1106) comprising a PCIe interface (1107) that interfaces with an FGPA (1108). The FPGA is coupled to DRAM (1109) and static random-access memory (1110—SRAM) (e.g., 1 GB DRAM and 18 MB SRAM in the illustrated example).

Figure 12:
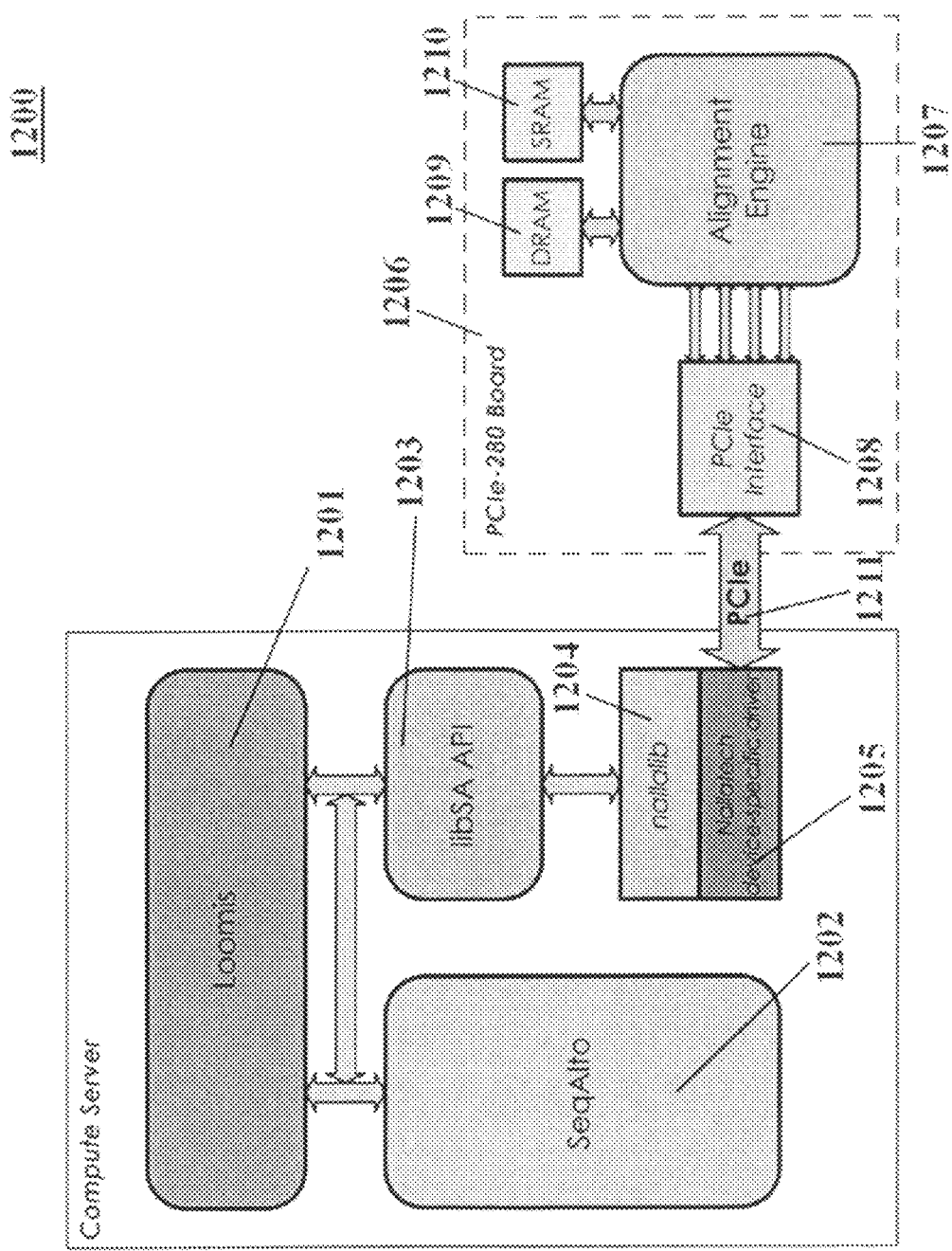

FIG. 12 shows an example hardware configuration 1200, in accordance with an embodiment of the invention. A computer server (1201) is programmed to execute machine-executable code implementing the SeqAlto algorithm (1202). The server also is in communication with a libSA API (1203) that is in communication with nallalib (1204) and a device-specific driver (1205). Via a PCIe communications bus (1211) and alignment engine on a PCIe-280 board (1206), the hardware configuration of FIG. 12 can perform alignment on raw genetic sequence data. In some cases, the alignment engine (1207) is mounted on a PCIe-280 board that comprises a PCIe interface (1208) in communication with an FPGA linked to DRAM (1209) and SRAM (1210), similar to that shown in FIG. 11.

Figure 13:
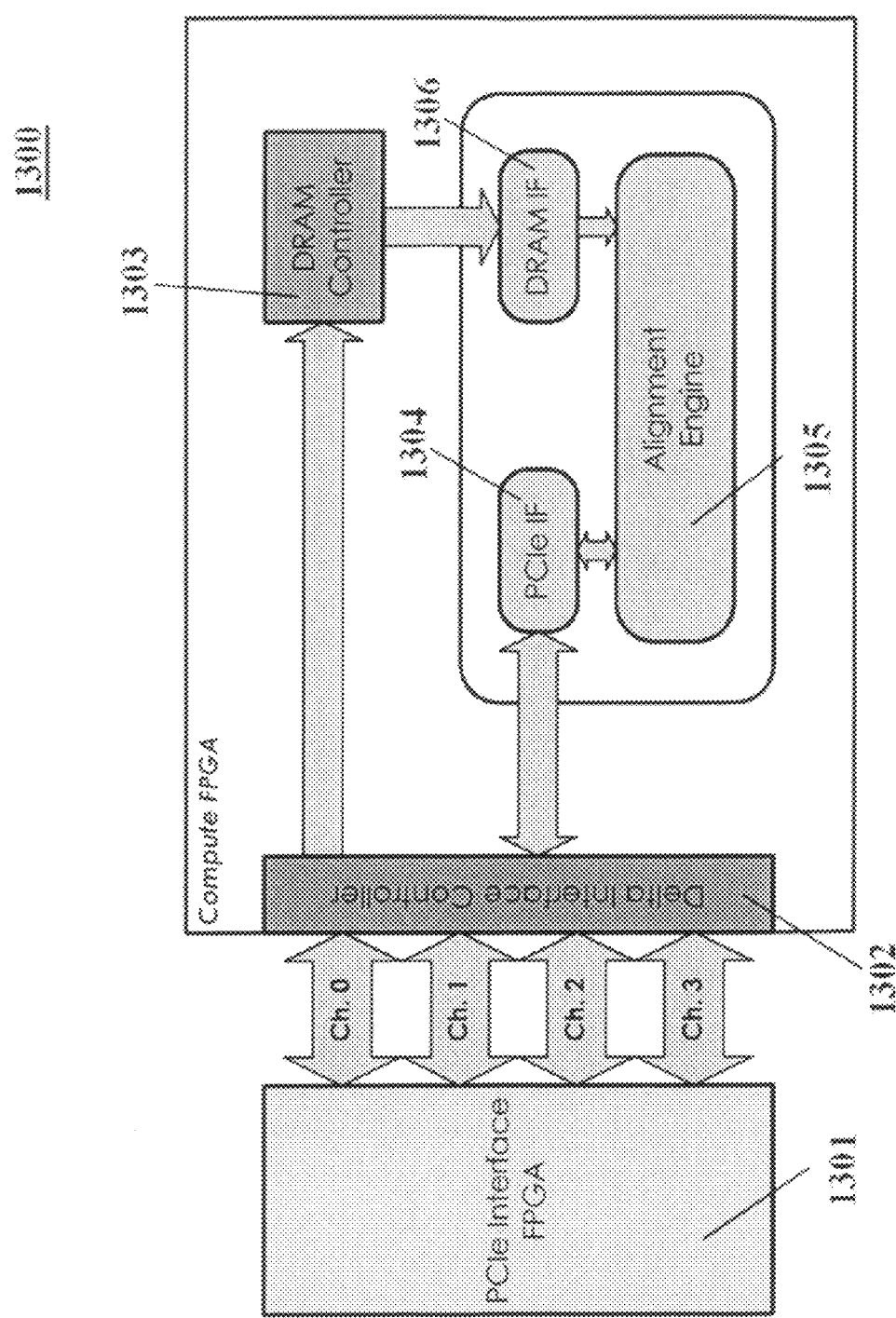

FIG. 13 shows an example hardware acceleration stack configuration (1300), in accordance with an embodiment of the invention. A PCIe interface FPGA (1301) is in multi-channel communication with a delta interface controller (1302) that, in turn, is in communication with a DRAM controller (1303) and a Peripheral Component Interconnect Express (PCIe) module (1304). The PCIe IF module (1304) is in communication with an alignment engine (1305) that is configured to perform alignment on raw genetic sequence data. The DRAM controller (1303) is in communication with a DRAM IF module (1306) that is in communication with the alignment engine.

Figure 14:
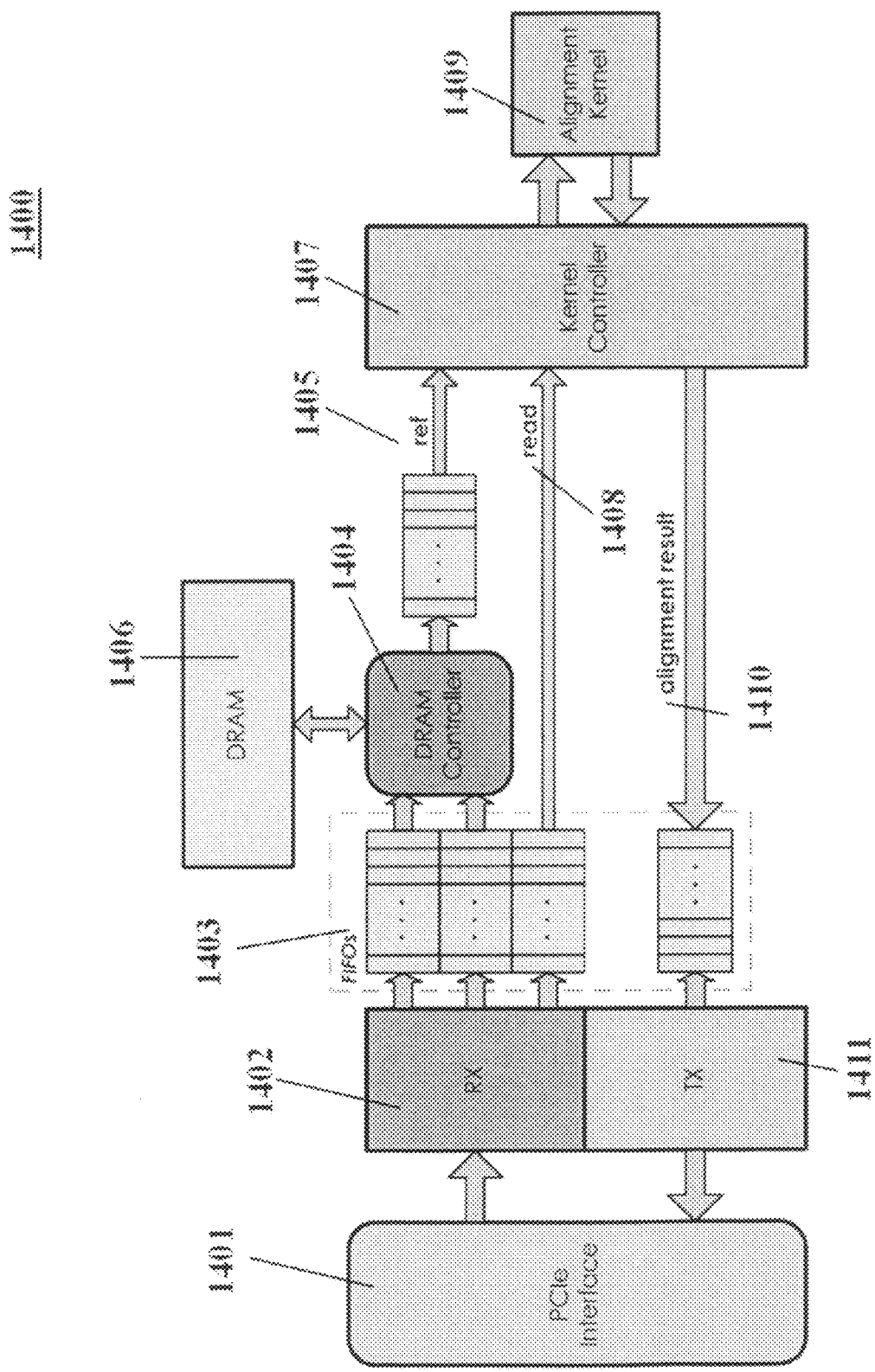

FIG. 14 schematically illustrates an example alignment engine 1400, in accordance with an embodiment of the invention. Raw data is entered into the alignment engine via a PCIe Interface (1401) and passes to a receiver (1402) module that queues the raw sequence read data for alignment in a FIFO configuration. The queuing of raw sequence data is communicated to a DRAM controller (1404) that accesses reference reads (1405) from the DRAM memory (1405) that are then communicated by the DRAM controller to the kernel controller (1407). The queued raw sequence data (1408) is also transferred to the kernel controller. The kernel controller initiates the alignment kernel (1409) which comprises one or more algorithms and performs the alignment using the raw sequence reads and the reference reads. The result of the alignment (1410) is transferred back to a transmitter (1411) in a FIFO configuration, which communicates the result back to the PCIe interface (1401) for downstream use (e.g., variant analysis, output to user, etc.).

Figure 15:
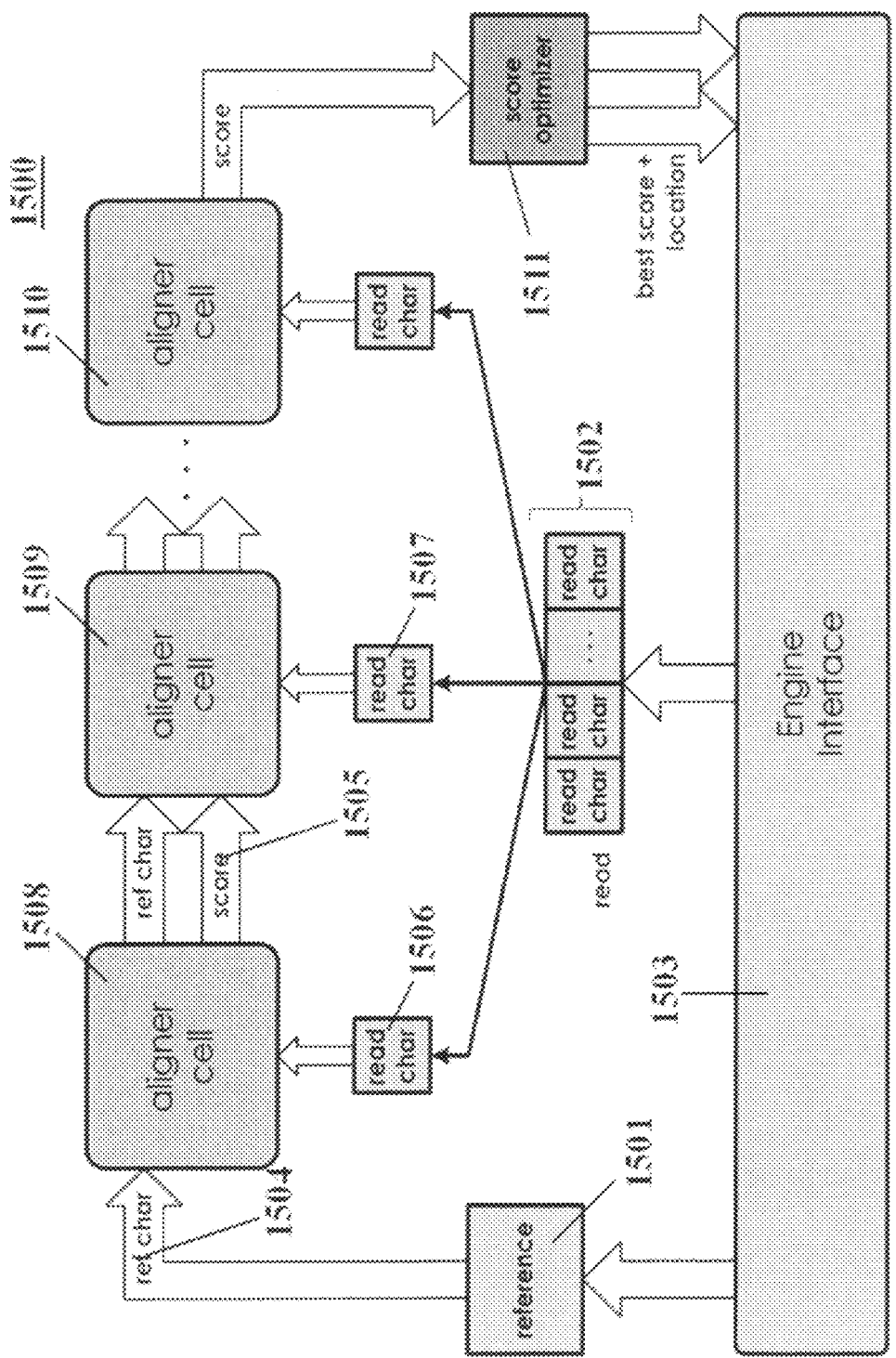

FIG. 15 schematically illustrates the implementation of an alignment algorithm by an alignment engine, such as that shown in FIG. 14, in accordance with an embodiment of the invention. A reference read (1501) and a raw data read (1502) are read into the alignment engine via an engine interface (1503). Each base of the reference read (1504) is compared, via a score (1505), with a base of the raw data read (1506) in an aligner cell (1508). After a score is computed, the reference character is then passed to a next aligner cell (1509) for comparison, via another score, with another base (1507) of the raw data read until all bases of the read have been compared. The obtained scores are passed from the final aligner cell (1510) and entered into a score optimizer (1511) that determines the best score and location of that score for alignment.

Figure 2:
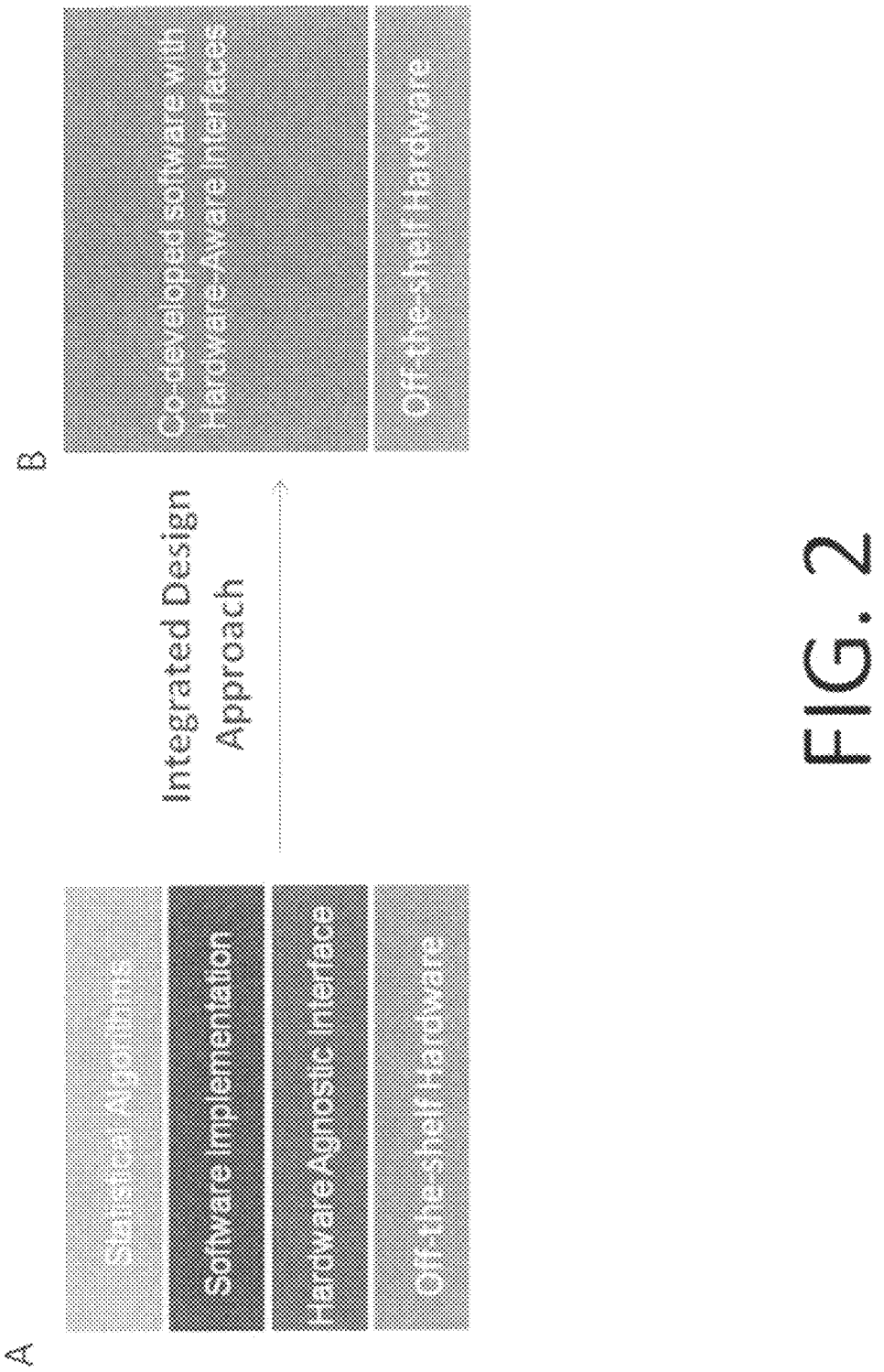
FIG. 2 depicts a schematic diagram of the platform, in accordance with an embodiment of the invention.

In some embodiments, an integrated hardware/software platform comprises an FPGA framework and is API (Application Programming Interface) build. In some embodiments, the platform additionally comprises Compute Hardware Design, system software and user interface, firmware software, and bioinformatics applications, such as, e.g., algorithms for re-sequencing applications and Bayesian inference. FIG. 2 depicts a schematic of an example integrated hardware/software platform that may be used for sequence data compression and analysis. As compared to other platforms that may utilize algorithms (e.g., statistical algorithms, software implementation, etc.) developed using hardware agnostic interfaces (FIG. 2A), some embodiments provide a platform that utilizes algorithms and software developed and optimized to run on systems provided herein using hardware aware interfaces (FIG. 2B).

Figure 9:
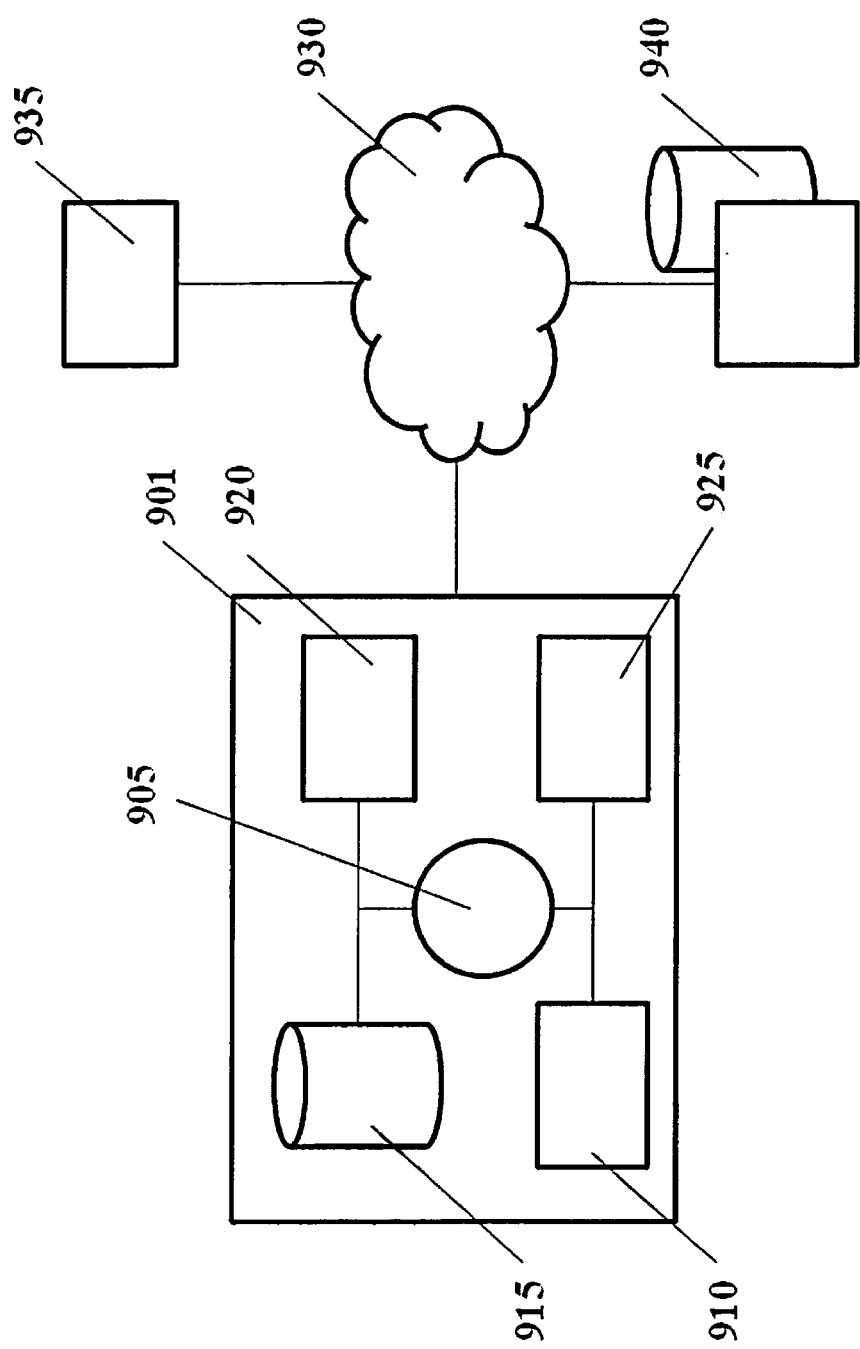
FIG. 9 shows a system for processing genomic sequence information, in accordance with an embodiment of the invention.

FIG. 9 shows an example hardware/software platform that comprises a central computer server ("server") 901, in accordance with an embodiment of the invention. The server 901 is programmed to implement the methods of the invention, such as communicating with a nucleic acid sequencer and receiving raw sequence data for processing and analysis. The server 901 includes an electronic control unit 905, such as a central processing unit (CPU, or "processor"), an field-programmable gate array (FPGA), or a programmable logic device (PLD). The electronic control unit 905 can include a plurality of CPU's, FPGA's or PLD's. In some situations, the electronic control unit 905 is a single core or multi core processor, or a plurality of processors for parallel processing. The server 901 also includes memory 910 (e.g., random access memory (RAM), read-only memory (ROM), flash memory), electronic storage unit 915 (e.g., hard disk), communications interface 920 (e.g., network adapter) for communicating with one or more other systems, and peripheral devices 925, such as cache, other memory, data storage and/or electronic display adapters. The memory 910, storage unit 915, interface 920 and peripheral devices 925 are in communication with the electronic control unit 905 through a communications bus (solid lines), such as a motherboard. The storage unit 915 can be a data storage unit (or data repository) for storing data. The server 901 is operatively coupled to a computer network ("network") 930 with the aid of the communications interface 920. The network 930 can be the Internet, an internet and/or extranet, or an intranet and/or extranet that is in communication with the Internet. The network 930 can include one or more computer servers, which can enable distributed computing.

The server 901 can be in communication with a sequencer 935 (e.g., Illumina sequencer, Ion Torrent sequencer). In some cases the serve 901 is in communication with the sequencer through the network 930. In other cases, the server 901 is directly connected to the sequencer 935, such as through a USB port or other connection.

In some situations, the server 901 is in communication with a remote computer system 940, which may be programmed for data processing and/or analysis. The remote computer system 940 can be programmed to sequence data as processed by the server 901. In some situations, the server 901 retrieves raw genomic sequence ("sequence") data from the sequencer 935 and processed the data. The processed data is subsequently stored on the remote computer system 940 for subsequently processing and/or analysis.

In some situations, the server 901 retrieves raw sequence data and processes the data. The server 901 then stores the data on the remote system 940. The data, as processed and stored on the server, has an aggregate size that is reduced by a factor of at least 1.5, 2, 3, 4, 5, 6, 7, 8, 9, 10, 100, 1000, 10,000, 100,000, 1,000,000 in relation to the raw data from the sequencer 935.

In some situations, the server 901 can be provided in a system adapted to enable the processing of sequence data in a serial and/or parallel configuration. The system can include multiple individual servers provided in a modular configuration.

In some embodiments, the server 901 is programmed to process raw genetic sequence data to yield processed data that is reduced in size. In some situations, upon processing, the raw genetic sequence data, having a size on the order of gigabytes, terabytes, or larger, is reduced to a size on the order of at least $\frac{1}{10}$, $\frac{1}{100}$, $\frac{1}{1000}$, or $\frac{1}{10,000}$ of a terabyte without loss of data integrity.

Figure 10:
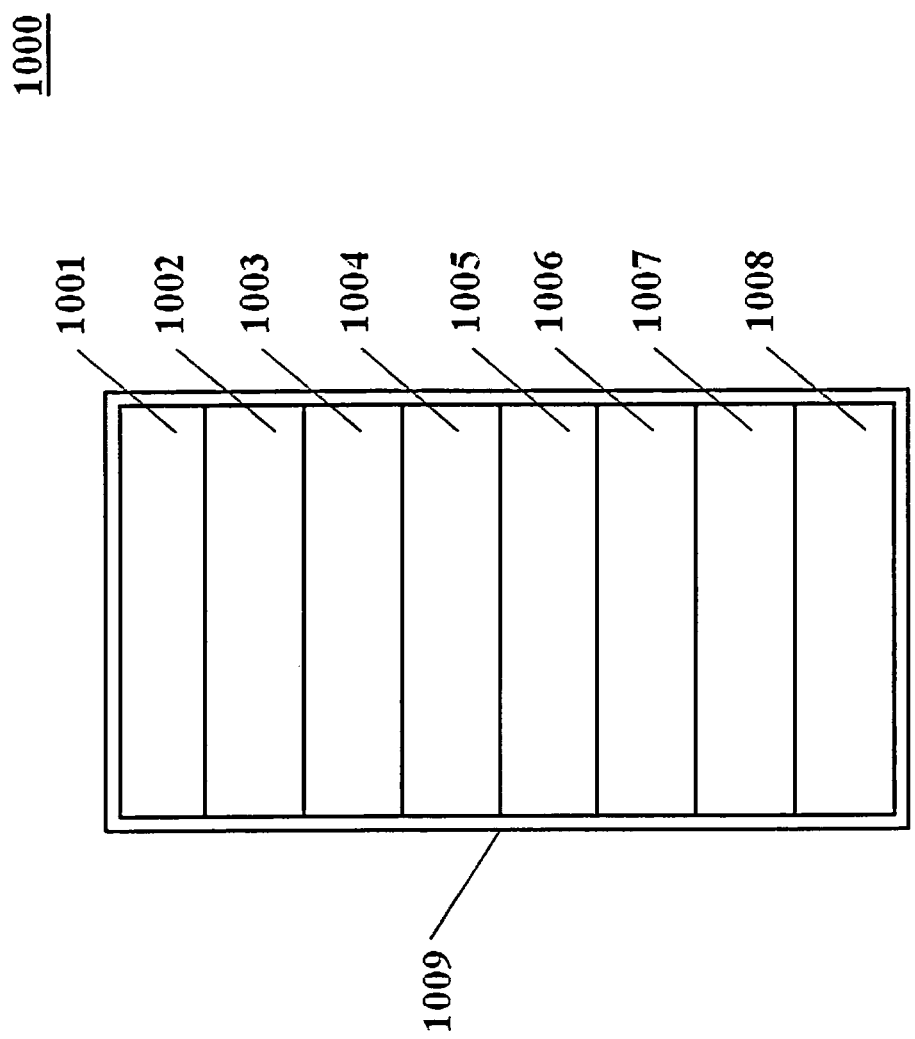
FIG. 10 shows a system having a plurality of servers, in accordance with an embodiment of the invention.

FIG. 10 illustrates a system 1000 having a plurality of servers 1001, 1002, 1003, 1004, 1005, 1006, 1007 and 1008 mounted on a housing 1009. The servers 1001-1008 can be removable mounted on the housing 1009, or in some cases permanently mounted on the housing 1009. The servers 1001-1008 can each be identical to the server 901 of FIG. 9.

The severs 1001-1008 can each receive raw sequence data from a sequencer and processes the sequence data. Such processes data can subsequently be stored on a remote computer system. In some situations, the servers 1001-1008 processes raw sequence data in parallel—i.e., each server 1001-1008 processes a select portion of raw sequence data. The servers 1001-1008 may process sequence data in a serial configuration, in which case a subset of the servers 1001-1008 processes raw sequence data for subsequent processing and/or analysis by another subset of the 1001-1008.

Methods of the present disclosure can be implemented by way of machine (or computer processor) executable code stored on an electronic storage location, such as, for example, on the memory 910 or electronic storage unit 915. During use, the code can be executed by the electronic control unit 905. In some cases, the code can be retrieved from the storage unit 915 and stored on the memory 910 for ready access by the electronic control unit 905.

Aspects of the systems and methods provided herein, such as the server 901, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such memory (e.g., ROM, RAM) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

In some cases, the server 901 can be configured for data mining and extract, transform and load (ETL) operations, which may permit the system to load information from a raw data source (or mined data) into a data warehouse. The data warehouse may be configured for use with a business intelligence system (e.g., Micro Strategy®, Business Objects®).

Information (e.g., instructions, processed nucleic acid sequence data) can be presented to a user on a user interface (UI) of an electronic device of the user or a system for processing data, as described elsewhere herein. Examples of UI's include, without limitation, a graphical user interface (GUI) and web-based user interface. The UI (e.g., GUI) can be provided on a display of an electronic device of the user. The display can be a capacitive or resistive touch display. Such displays can be used with other systems and methods of the disclosure.

Methods of the disclosure can be facilitated with the aid of applications (apps) that can be installed on electronic devices of a user. An app can include a GUI on a display of the electronic device of the user. The app can be programmed or otherwise configured to perform various functions of the system.

Systems of the present disclosure may be programmed or otherwise configured for machine learning. This may provide for more efficient or optimum alignment and analysis (e.g., variant analysis) of genetic sequence data. Various machine learning algorithms may be employed for use with systems and methods of the disclosure, such as, for example, decision tree learning, association rule learning, artificial neural networks, genetic programming, inductive logic programming, support vector machines, clustering, Bayesian networks, reinforcement learning, representation learning, similarity and metric learning, and sparse learning. A support vector machine (SVM) algorithm of the disclosure can be a supervised learning model with associated learning algorithms that analyze genetic sequence data and recognize patterns in the data, which can be used for classification and regression analysis. An SVM can take a set of input data (e.g., raw genetic sequence data) and predict, for each given input, which of two possible classes forms the output, making it a non-probabilistic binary linear classifier.

The machine learning algorithm can be a trained algorithm. A machine learning algorithm, such as an SVM, can use a set of training examples, each marked as belonging to one of two categories. The SVM training algorithm can then build a model that assigns new examples into one category or the other. An SVM model can be a representation of the examples as points in space, mapped so that the examples of the separate categories are divided by a clear gap that has a given width. New examples are then mapped into that same space and predicted to belong to a category based on which side of the gap they fall on.

Figure 3:
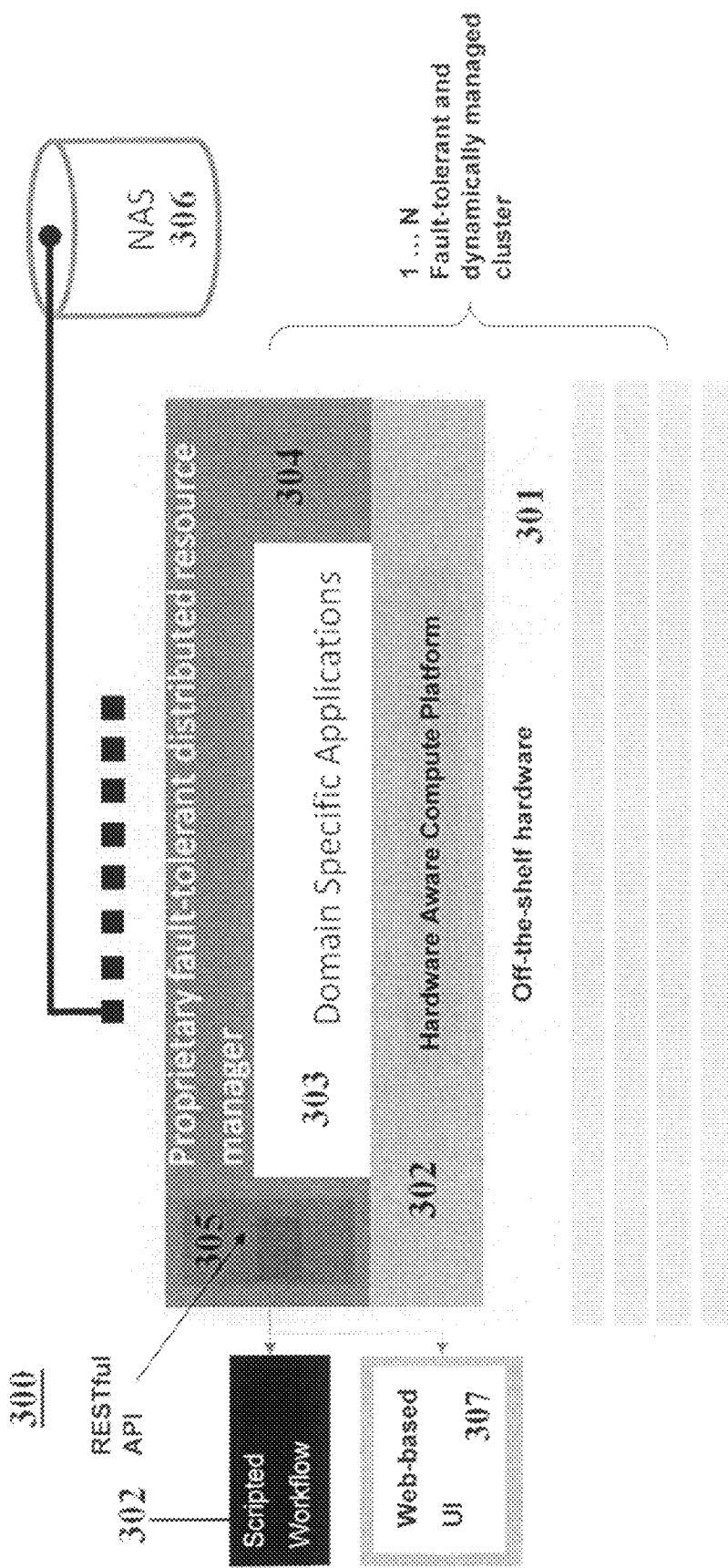
FIG. 3 depicts a more detailed schematic of platform architecture.

FIG. 3 schematically illustrates an example integrated hardware/software platform (300), in accordance with an embodiment of the invention. The platform includes off-the-shelf hardware (301) that utilizes a hardware aware interface (302). The platform includes domain specific applications (303), a fault-tolerant distributed resource manager (304) and a Restful application programming interface (API—305). The platform is capable of sending data stored on or generated by the platform on a networked attached storage (NAS) device (306). Users interact with the platform via a web-based user-interface (UI—307). In some cases, platform 300 utilizes a scripted workflow (308). The platform 300 can include one or more modules mountable on a support structure, each module adapted to process data from a genomic sequencer (e.g., Illumina sequencer, Ion Torrent sequencer) and output processed data for subsequent analysis. The modules can operate in parallel—e.g., raw sequence data can be distributed among a plurality of modules and perform various tasks (e.g., alignment, variant analysis, structural variant analysis, etc.)—or operate sequentially—e.g., a first module can processed sequence data, and a second module can analyze the processed data from the first module.

Figure 7:
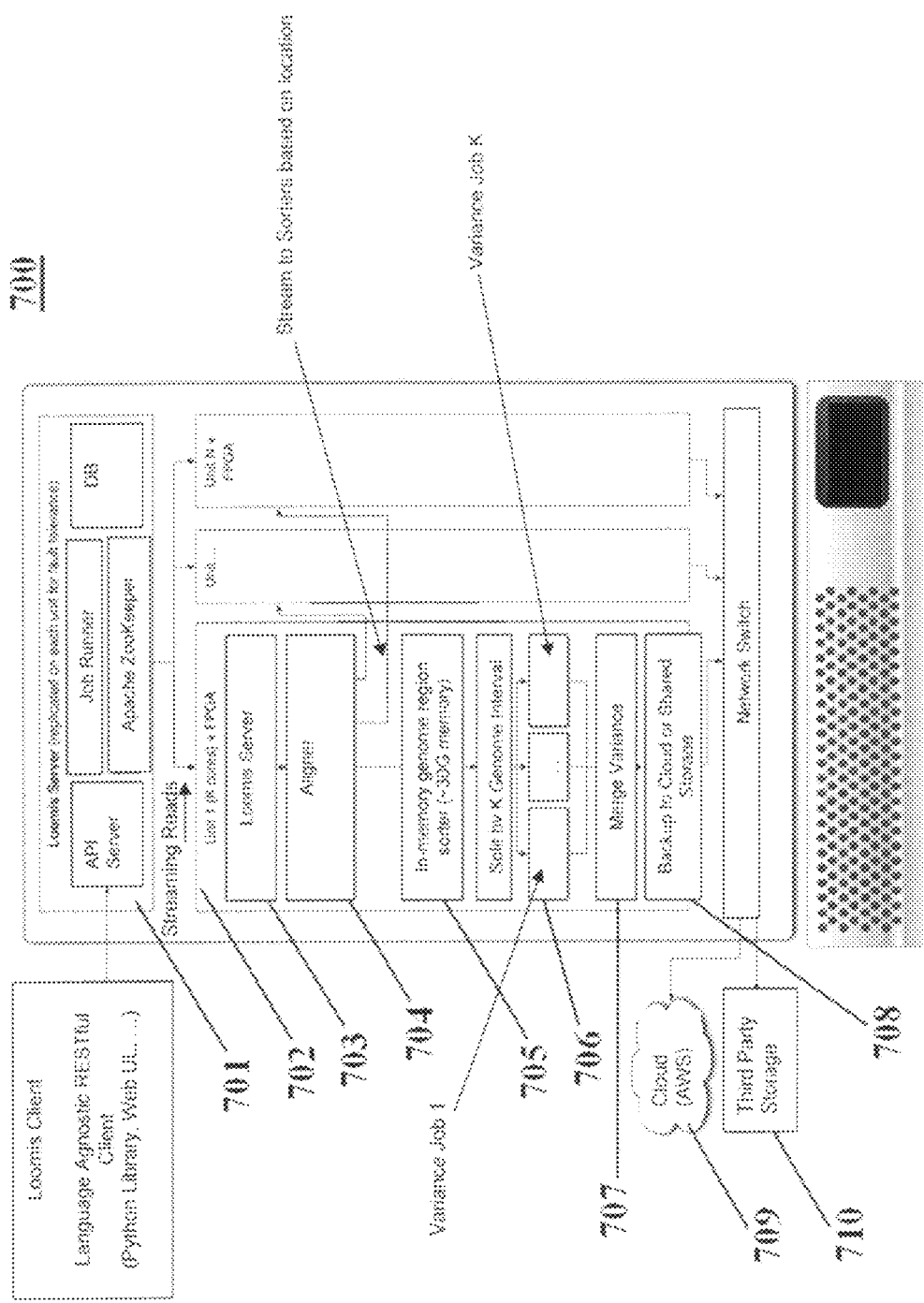
FIG. 7 shows an integrated hardware/software platform, in accordance with an embodiment of the invention.

FIG. 7 schematically illustrates an example modular platform 700 configured to process genetic sequence data, in accordance with an embodiment of the invention. The system 700 includes a server (701) communicatively coupled to one or more nodes 702, each node having an integrated circuit, such as a field programmable gate array (FPGA) (e.g., Xilinx, Alter), other logic (e.g., programmable logic device), or one or more central processors. Each node (702) includes a server (703) and several modules that include an alignment module (704)), an in-memory genome region sorter module (705), variance analysis module (706), a merge variance module (707) and a backup module (708) module. The system 700 includes an interface that communicatively couples the system 700 to the cloud (709), and/or other third-party storage (710), which can include one or more external servers for data storage and/or processing. In the case of a failed job (e.g., failed alignment), a server may need to re-run a job from the beginning. In some embodiments, the system 700 includes at least 1, 2, 3, 4, 5, 6, 7, 8, 9, 10, 20, 30, 40, 50, 100, 1000, or 10,000 modules.

An exemplary operation of the system 700 is illustrated in FIG. 7, in which the arrows illustrate the direction of data flow. Data from a genetic sequencer (e.g., Illumina sequencer) is distributed to each node 702 of the system. If the system 700 includes a plurality of nodes, the data is distributed among the plurality of nodes. In some cases, a portion of the data is distributed among each of the nodes. Next, a node directs genetic sequencing data to the aligner module (704), which aligns individual segments of the genetic sequence data to yield aligned data. The aligned data is subsequently analyzed, such as by variant analysis (in variant analysis module 706) and structural variant analysis (in variant analysis module 706), to yield analyzed data that is related to the genetic sequence data. In some situations, the aligned data and/or analyzed data is directed to a remote computer system, such as a remote server, which makes the aligned data accessible to one or more users. The remote server can be located at a location that is separate from the system 700, such as a separate facility.

Bottlenecks in distributing (or "job-scheduling") a desired computation (e.g., sequence alignment, variant analysis, etc.) may result in very high latency per sample—sometimes on the order of weeks. Moreover, heavy reliance on a shared file system such as network file system (NFS) share may result in rapid performance drops.

Servers described herein minimize the latency per WGS analysis while efficiently utilizing underlying resources. Latency is minimized by implementing a fault-tolerant and highly scalable distributed system such as that shown in FIG. 7 that enables concurrent usage of multiple nodes per analysis while maximizing the resource usage on all nodes.

Latency may be reduced by, for example, concurrently splitting the data for a sample while performing alignment; concurrently redistributing the aligned reads to variant calling engines; relying on local storage on each node to write intermediate files instead of shared storage; equally distributing reads based on equal partitioning of genomic regions among a cluster of nodes and the number of aligned reads on each node; using a sorter and aligner capable of utilizing large memory nodes to accelerate data input by reading data from network directly to memory (distributed memory management); and the inclusion of a distributed real-time monitoring engine for all nodes on a cluster and/or a Restful server-client model for user interaction.

As shown in FIG. 7, a server (701) may be independently installed globally on a platform and on multiple nodes. Such a configuration may scale up to any configurable number of nodes. A server may be designed for fault-tolerance, wherein if a node becomes inoperable, the server adapts to keep the remaining nodes of the cluster functioning. Fault-tolerance may be achieved by using a leader-follower cluster coordination technique. When the nodes are activated, the nodes may use an election algorithm (e.g., ZooKeeper) to elect one of the nodes as a "leader". From then on the leader may tells the other nodes what to do. In the case that the leader becomes inoperable, the remaining nodes may be notified and another leader may be elected amongst themselves.

Moreover, a server described herein may use curator (e.g., Netflix Curator) to interact with an election algorithm, in order to provide additional distributed locking algorithms to work in concert with the election algorithm.

Figure 24:
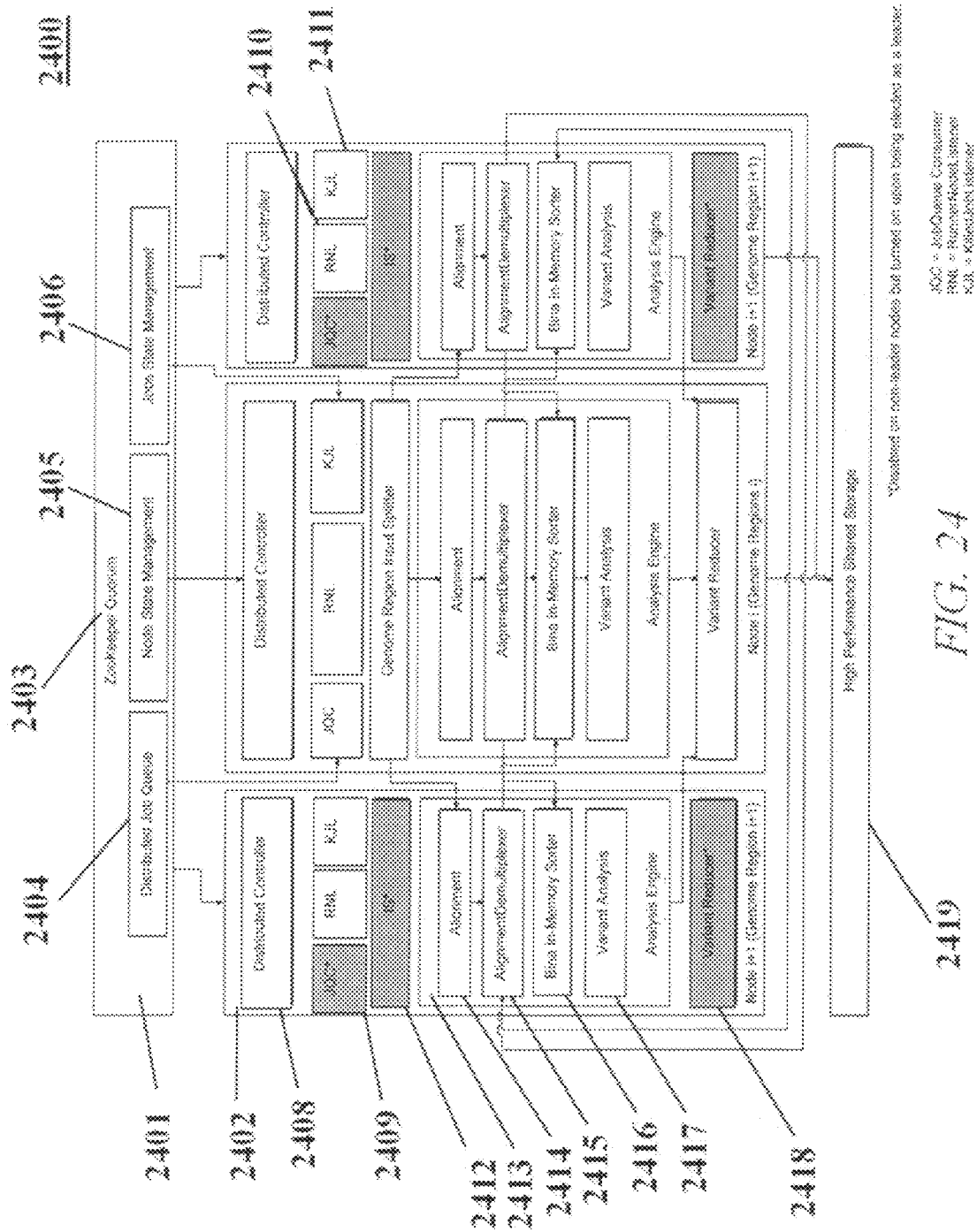
FIG. 24 shows an example of a Loomis analysis diagram.

FIG. 24 schematically illustrates another example modular platform 2400 comprising a server 2401 communicatively coupled to several nodes 2402 configured to align raw sequence data and perform variant analysis. While the example platform in FIG. 24 depicts only three nodes, any number of nodes may be used. The server utilizes an open-source distributed coordination algorithm (2403), a distributed job queue (2404 i.e., a list of jobs that are queued to run on the server using a first-in-first-out (FIFO) strategy); node state management (2405 i.e., a group of distributed coordination algorithm nodes that may be used to define the state of each node of the server and used to elect a "leader" between nodes); and job state management (2406 i.e., a group of distributed coordination algorithm nodes that are used to define the state of jobs to be communicated between nodes of the platform).

As shown in FIG. 24, each node of the platform may comprise any of the following modules:

a. A distributed controller module (2408) responsible for communicating with the distributed coordination algorithm of the server for, such as, leader election.
b. A job queue consumer (2409—JQC) module that listens for jobs that are added to the job queue. In some cases, the JQC is active on the leader node and is inactive on the followers. Upon election of a new leader node, the JQC may then be activated on the new leader node.
c. A runner node listener (2410—RNL) module that listens for communication messages from the leader node.
d. A killed job listener (2411—KJL) module that permits a node to communicate with others when a job fails and coordinate node clean-up after a failed job.
e. An input splitter (2412—IS) module that is capable of reading input FASTQ (a commonly used file format used by sequencers to record raw data) files from a high performance shared disk and equally broadcasting the data to all nodes to balance the load of data to be aligned between each node. As with the JQC, the IS may be active on the leader node and inactive on the followers. Upon election of a new leader node, the IS may then be activated on the new leader node. The IS may also be capable of equally partitioning a reference genome. Each node may be assigned to perform variant analysis on a specific genomic region to balance variant calling between each node.
f. An analysis engine module (2413) capable of performing analysis on data. An analysis engine module may comprise a variety of its own modules that include:
  i. An aligner (2414) a module that may be used to align raw data, using one or more alignment algorithms/engines, including those described herein. Reads for alignment may be received concurrently via network sockets from a leader node and aligned using aligner. In some cases, no data is written to disk.
  ii. An alignment demultiplexer (2415): a module that sends aligned reads to nodes responsible for performing variant analysis on the specific region they are aligned. Sometimes, communication between nodes occurs via network sockets. Moreover, in some cases, no data is written to disk.
  iii. In-memory sorter (2416): a module capable of receiving and sorting aligned reads from all aligners running in the platform. In some cases, the in-memory sorter communicates via network sockets. Moreover, aligned read data may be kept in memory to improve data aggregation and sorting speeds.
  iv. A variant analysis module (2417): a module capable of performing variant analysis using one or more variant analysis tools or algorithms. Aligned data may be output from an In-Memory Sorter and written to a local disk that may be accessed by the variant analysis module. In some cases, a multithreaded variant analysis is run on the genomic region under investigation in each node.
g. A variant reducer (2418) module that compiles variant analysis results from all nodes of the platform to generate a final set of variant calls (e.g., SNP, Indels, and SV). The variant reducer module is generally activated on the leader and activated on a new leader when one is elected.
h. A high performance shared storage (2419) module in which results from variant calls are written, in addition to any other appropriate log files.

In some cases, a user may interact with the platform shown in FIG. 24 via a Restful API server (not shown) that is located on each node. This configuration may be used for fault-tolerance. Moreover, the API server may be activated on a node only when a node has been selected as a leader A server, such as that shown as 2401 in FIG. 24 may also include a software development kit (SDK) that enables a developer to write his/her own custom script to control the flow of data through the platform and/or the configuration of any of the platform components, including the server. One example of an SDK that may be used is a PythonSDK.

The type of hardware used for a modular platform may vary, depending on, for example, the performance of the platform desired. In some embodiments, a modular platform may comprise independent, scalable compute nodes. Each node can be, for example, a 1 U (1.75 in./44.45 mm) rackmount server based around two hex-core hyperthreaded CPUs running at 3.06 GHz and 96 Gb of DDR (dynamic data rate) 3-1333 dynamic random access memory (DRAM). In some cases, this configuration gives 24 threads per node, with a peak memory bandwidth of 64 Gb/s.

In some embodiments, a modular platform may comprise a four-node/4 U cluster interconnected using an 24-port non-blocking Gigabit Ethernet switch. With each node using two network ports, the switch can allow expansion up to twelve nodes if external network connectivity is provided through a dedicated SFP+ uplinks.

In some examples, a platform may comprise an Ethernet switch, a power distribution unit, and/or be disposed in a casing to create a self-contained appliance. In one example, a four-node system is packaged with an Ethernet switch and a power distribution unit in a 7 U enclosed cabinet measuring 24"×24"×36". In some embodiments, the appliance requires only a 20 A power circuit. In some cases, the appliance utilizes a network connection.

In some examples, user data storage is provided on three 300 GB 10,000 RPM SATA hard drives. Moreover, a platform may comprise a gigabit Ethernet interface.

Example Platform Performance

The performance of a particular platform may vary, depending, for example, on the availability of hardware, type of hardware, configuration of the platform, the algorithms used, and combinations thereof.

A challenge of processing genomic sequence data is the size of the raw data files, which can be in the 500 GB-terabyte (TB) range. In some cases, one 2-hour run on a Solexa sequencing machine can generate 320 TB of data. The large size of genomic sequence data may require vast computing resources and time for storage and analysis. In some embodiments, a platform described herein may reduce the size of sequence datasets without loss of information.

In some cases, a platform described herein may be capable of compressing raw sequence data by at least about 10 times ("×"), 20×, 40×, 60×, 80×, 100×, 200×, 400×, 600×, 800×, or 1000× without loss of information. In some cases, the platform compresses sequence data by 10-100×, 40-400×, 60-600×, or 100-1000× without loss of information.

The capability of a platform to align reads of a given length may vary. In some embodiments, a platform described herein may be capable of aligning reads ranging from about 20 to more than 5 million ("M") nucleotides in length without loss of fidelity or speed. In some embodiments, the platform is capable of aligning reads ranging from about 20-100 base pairs ("bp"), 50-200 bp, 100-500 bp, 200-1000 bp, 500 bp-2 kilobase pairs (Kbp), 1000 bp-5 Kbp, 2 Kbp-1-mega-bp (1 Mbp), 5 Kbp-5 Mbp, or more than 5 Mbp. In some aspects, the platform is capable of aligning single end reads or paired end reads.

One bottleneck in sequence alignment may be the amount of time required to align a large number of reads with an acceptable error rate (typically about 5% or less). Platforms described herein may be capable of fast sequence alignment times, with acceptable error rates. For example, a platform described herein may be capable of aligning up to about 1 billion reads in less than or equal to about 2 days. In some embodiments, a platform described herein may be capable of aligning up to about 1 billion reads in less than or equal to about 1 day, or less than or equal to about half a day. In some embodiments, a platform described herein may be capable of aligning up to about 1 billion reads in less than or equal to 5 hours. In some embodiments, the platform is capable of aligning up to about 1 billion reads in less than or equal to 2.5 hours. In some embodiments, the platform is capable of aligning up to about 1 billion reads in less than or equal to about 1 hour. In some embodiments, the platform is capable of aligning up to about 1 billion reads in about 30 minutes.

The speed at which alignments are made by a platform may vary. In some embodiments, the platform can perform at least about 1 million alignments per second. In some embodiments, the platform can perform at least about 10 million alignments per second. In some embodiments, the platform can perform at least about 12 million alignments per second. In some embodiments, the platform can perform at least about 1 billion alignments per hour. In some embodiments, a platform can perform between about 200,000 and 12 million alignments per second.

The accuracy of an alignment may vary. In some cases, the platform can perform alignment of reads with at least about 95%, 96%, 97%, 98%, or 99% accuracy The presence of indels can present a challenge to sequence alignment. A platform described herein may be relatively fast and capable of accurately locating indels of large base numbers. In some embodiments, a platform described herein may be capable of reliably placing insertions and deletions from about 1 to 25 bp, with an accuracy greater than or equal to about 95%. In some embodiments, a platform can reliably place insertions and deletions with an accuracy greater than or equal to about 96%, 97%, 98%, or 99%.

Due to the large amount of data handled during alignment, alignment methods can require large availability of memory for execution. In some embodiments, a platform described herein is capable of aligning reads using less than or equal to 40 Gb of memory. In some embodiments, a platform is capable of aligning reads using less than or equal to 20 Gb, less than or equal to 15 Gb, less than or equal to 10 Gb, or less than or equal to 8 Gb of memory.

The time requirements to perform sequence alignment and variant analysis of a whole genome may vary. In some aspects, a platform described herein can perform high fidelity sequence alignment and variant analysis of a whole genome with about 30× coverage in about 24 hours or less. In some embodiments, the platform completes sequence alignment and variant analysis in about 12 hours or less. In some embodiments, the platform completes sequence alignment and variant analysis in about 6 hours or less. In some embodiments, the platform completes sequence alignment and variant analysis in about 4 hours or less.

The time requirements to perform sequence alignment, variant analysis, and structural variant analysis may vary. In some cases, alignment, variant analysis and structural variant analysis on the genomic sequence data with at least about thirty times coverage is completed in a time period less than or equal to about 5 hours, 4 hours, 3 hours, 2 hours, 1 hour, 0.5 hours, or 0.1 hours. In some embodiments, the time period is less than or equal to about 5 hours. In some embodiments, the time period is less than or equal to about 4 hours. In some embodiments, the time period is less than or equal to about 3 hours. In some embodiments, the time period is less than or equal to about 2 hours. In some embodiments, the time period is less than or equal to about 1 hour. In some embodiments, the time period is less than or equal to about 0.5 hours. In some embodiments, the time period is less than or equal to about 0.1 hours.

Figure 4:
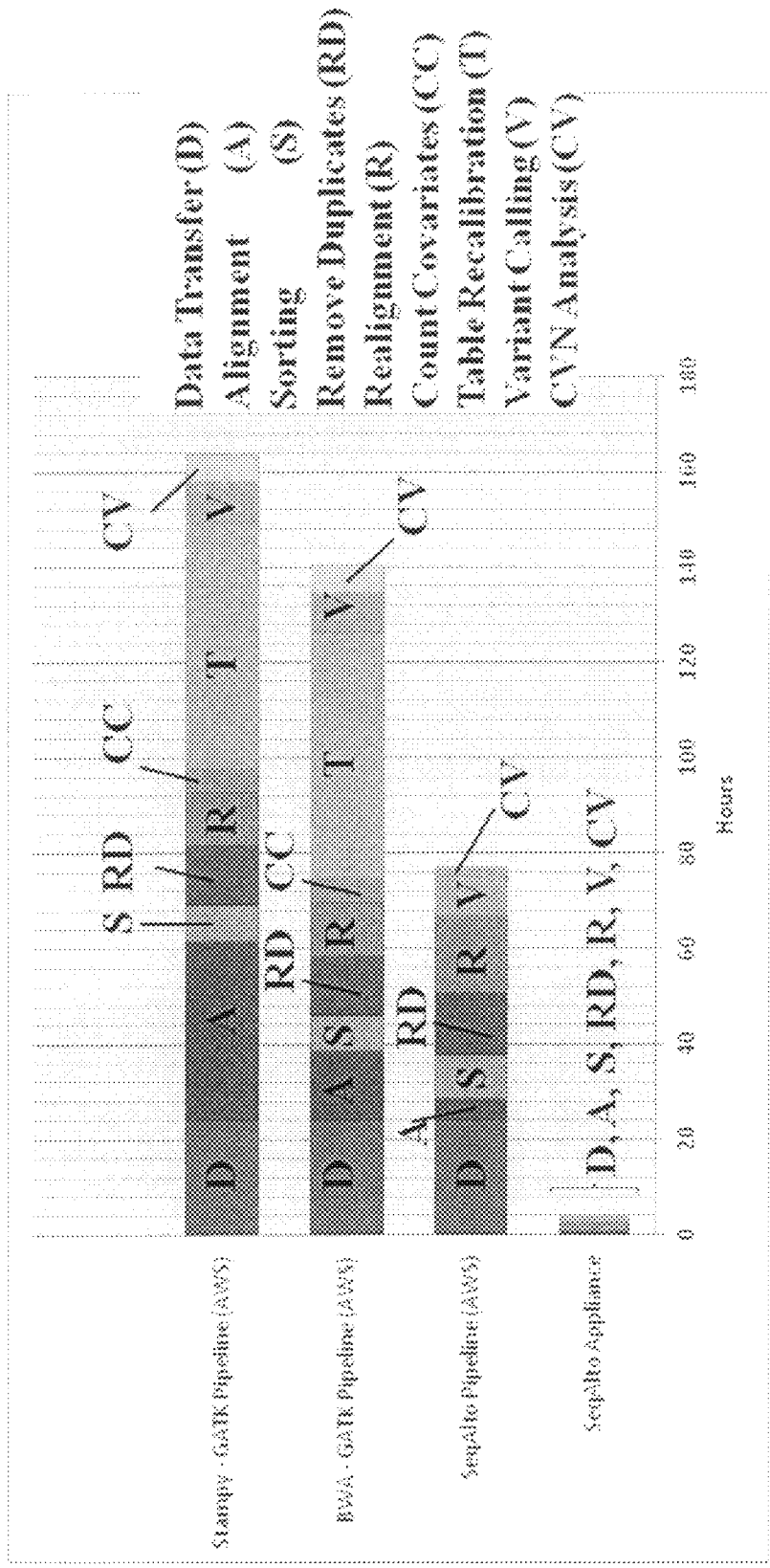
FIGS. 4-6 show stacked bar charts comparing total time for processing genome sequence data, with breakdown by individual functions, between the platform of the present invention (SeqAlto) and select other available technologies.
Figure 5:
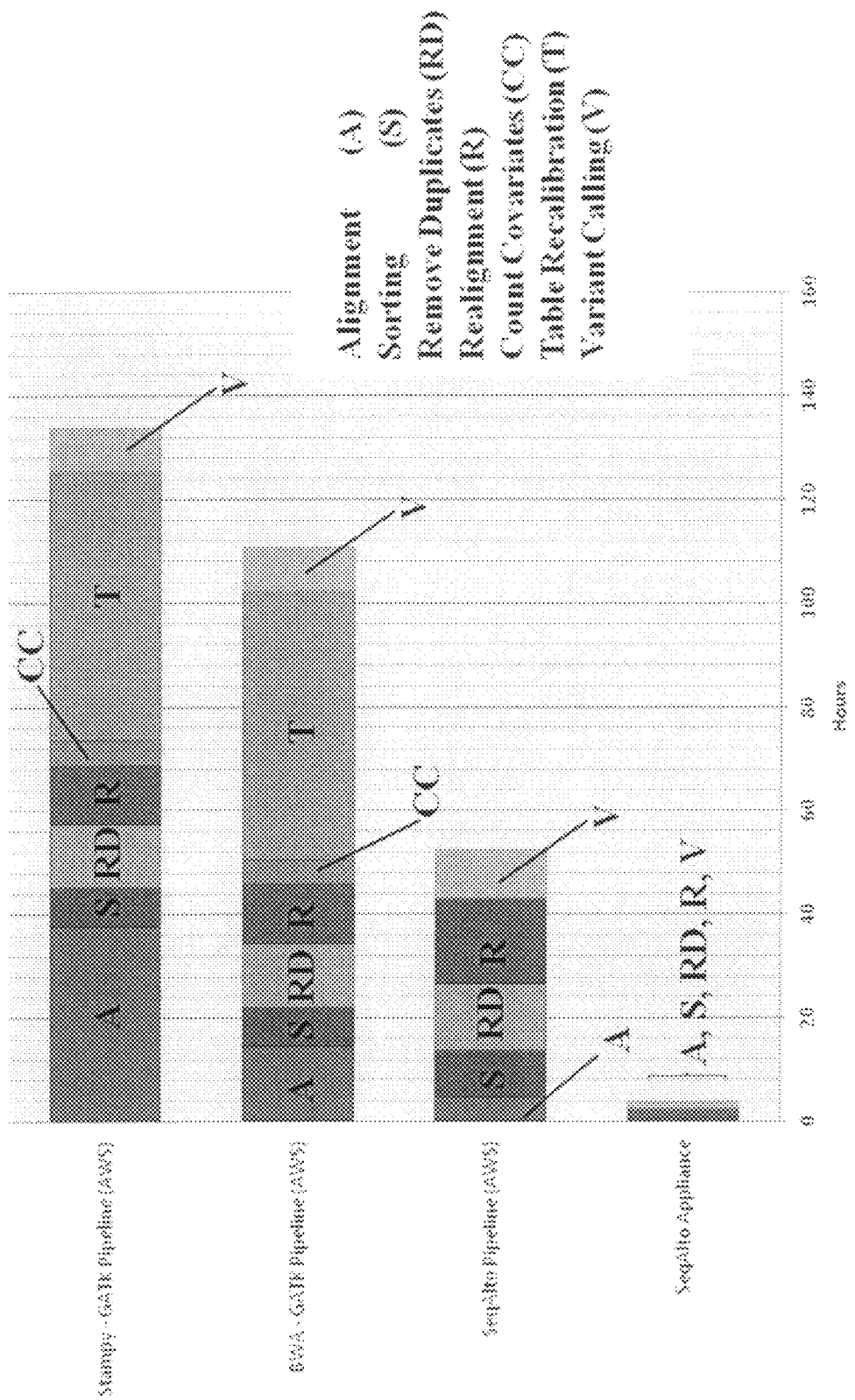
Figure 6:
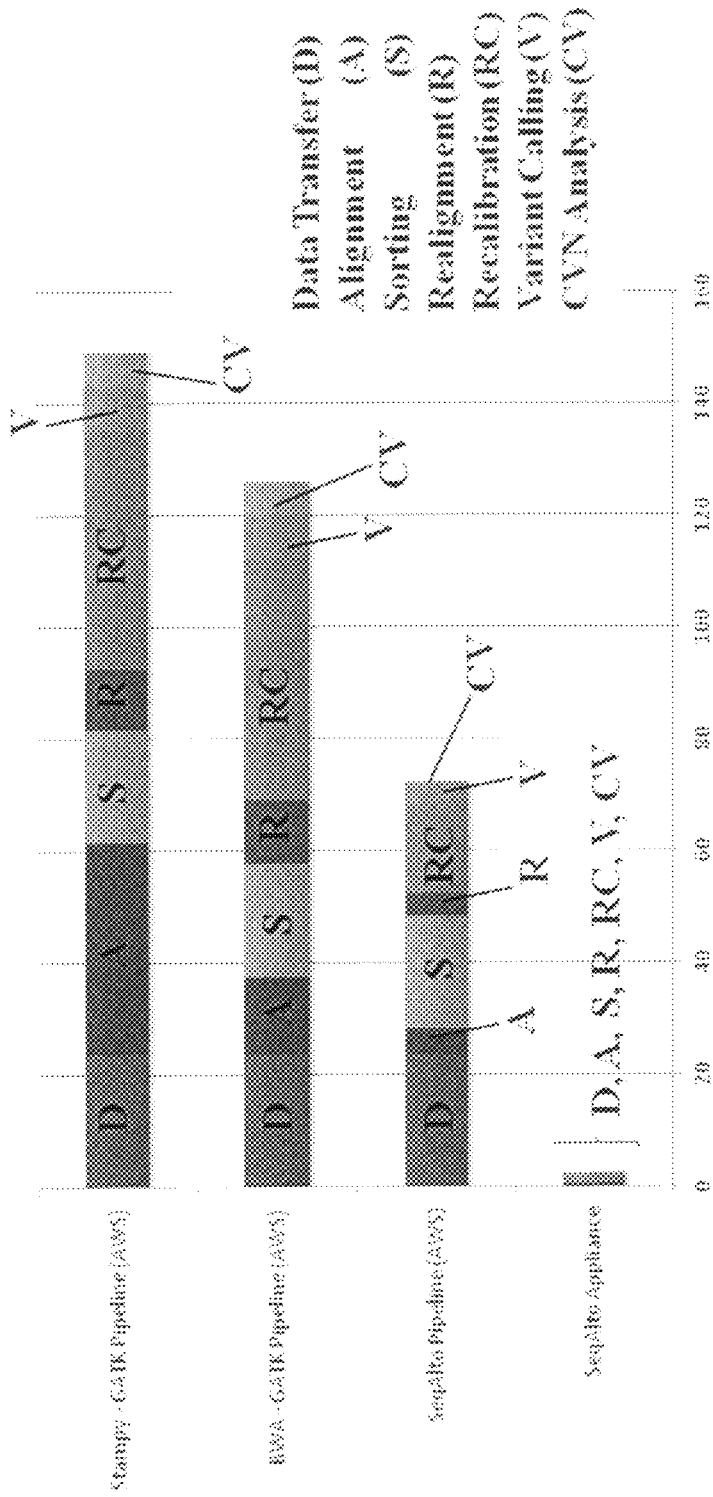

The integration of the software and hardware may improve the speed of processing and analysis of genome sequence data without loss of information or accuracy. In some embodiments, an integrated hardware/software platform improves the time required for processing sequence data by more than 2, 3, 4, 5, 6, 7, 8, 9, 10, 100, 1000, 10,000 or 100,000 fold. In experiments using simulated data and real Illumina read data, a platform including the methods described herein with hardware aware platforms, were compared to the algorithms of the present disclosure run using hardware agnostic platforms as well as other currently available algorithms run using the same hardware agnostic platforms. FIG. 4 illustrates the total time for processing and analysis of sequence data, broken down by individual bioinformatics platforms, including platforms of the present disclosure (e.g., SeqAlto pipeline and SeqAlto appliance). The SeqAlto appliance uses systems and methods of the present disclosure. FIGS. 5 and 6 illustrate exemplary total times for processing and analyzing a whole human genome with 30× coverage using platforms provided herein (SeqAlto) and other platforms (Stamey, BWA). In some embodiments, an integrated appliance using hardware aware platforms can reduce analysis time by more than 2, 3, 4, 5, 6, 7, 8, 9, 10, 100, 1000, 10,000 or 100,000 fold, as compared to the same algorithms used on hardware agnostic platforms, and reduces analysis time by over than 2, 3, 4, 5, 6, 7, 8, 9, 10, 100, 1000, 10,000 or 100,000 fold compared to currently available algorithms performed using hardware agnostic platforms.

Optimization

The performance of systems and methods of the disclosure may be improved with the aid of various optimizations. Both software optimizations and hardware optimizations may be utilized.

In some embodiments, a platform may be comprised of additional tools (e.g., SamSorter, FastRealignment, and Combined Genotyper) which may eliminate the need for constant reading, writing, and indexing of intermediate results, each of which can affect processing times.

SamSorter

The SamSorter may perform addition and/or replacement of read groups, sorting of BAM files, and duplicate removal in one step. The SamSorter generally sorts BAM (a binary sequence alignment data file) files, writes and splits BAM files to disk, is capable of on the fly compression of BAM files to make the most of memory resources, and can remove read duplicates. Such an approach may address issues with long latency and compute time related to sorting and merging BAM files; long latency and compute time related to duplicate removal of BAM files; and balance load for downstream analysis.

In general, the SamSorter may include several stages, such as in-memory sorting, in memory compression and potential spilling to disk, duplicate removal, and generating outputs and writing to a disk.

The in-memory sorting stage may be responsible for reading records from a pipe or file and sorting incoming records. This phase may be utilized to improve CPU efficiency, and may allow a separate aligner to use all of a platform's CPU resources.

In memory compression may allow maximum usage of memory resources by on the fly compression of SAM records. Several data structures may be useful in in memory compression, with non-limiting examples that include a table, a store and buffer structure, pseudo-pointers, and spilling-to-disk structures.

The table may contain a linked list for each location, since reads may be inserted at the start head of a list in each bucket with an insertion time of O(1), helping with CPU efficiency.

The store and buffer structure may allow for compression of the records. As records are streamed in, they may be buffered into blocks of a given size. Once a size limit is reached these blocks are compressed and stored away. In some cases, multiple records are compressed at a time to achieve a desired level of compression and maintain the ability to access these records individually in a random order.

Pseudo-pointers may aid in referencing individual records in a block. Such pointers may consist of a tuple containing the block number and record number within the block. Using the block number, the correct block header may be found. Once this header is found, the record number may be used to find the correct offset into the uncompressed string of all reads in the block.

Spilling to the disk structures may allow software to work with input files of varied size. In cases where the software runs out of the memory for keeping sorted records, it may write sorted records to a disk for later reading and subsequent merging.

Duplicate removal generally involves marking duplicates. Records may be inserted at their duplicate position. Paired records may exchange the needed mate and duplicate score information prior to insertion in the table. Furthermore, records may be reordered to their actual sorting position with a small (and bounded) amount of memory during the writing phase Once all records have been read and inserted into the in memory table, or spilled to disk, the writing phase may begin. The writing phase may be responsible for generating N equally sized sorted output regions. Each of these output regions may be handled by a separate thread, allowing full usage of the disk bandwidth. Sorted data may then be split into N sorted regions, each of these regions is handled by a single thread. If the entire region has been traversed, the operation is done. For each location in the sorted region, the in memory and spilled records may be gathered and duplicates marked for these gathered reads. The gathered reads may be inserted into the middle position of the reorder buffer. The records from the last position of the reorder buffer may be written-out. The process may then return to checking if the entire region has been traversed.

Fast ReAlignment

At least some aligners map each read (or read-pair) independently, which may result in the reads covering a putative indel have several different fine-scale alignments. The Fast ReAlignment may be used to update fine-scale alignments to be in better agreement with one another, thereby facilitating identification of an indel.

Combined Genotyper

A Combined Genotyper may comprise a number of processes, including base quality score recalibration and SNP/indel genotyping. In some embodiments, recalibration detects and corrects for biases in the raw base qualities produced during sequencing, which has a substantial impact on SNP and indel calling. SNP and indel variants are then called using a probabilistic model. For each putative variant, the likelihood (i.e. the probability of the observed reads given the variant) can be computed using the map quality, base qualities, and base alignment quality (BAQ) scores for the reads covering the variant. In conjunction with a prior probability, determined using a database of empirically observed variation (e.g. dbSNP—single nucleotide polymorphism database), a posterior probability for the variant can be obtained. Putative variants with sufficiently high posterior probabilities can be called, and the posterior probability can be encoded as the variant quality score. By combining the two procedures together, the Combined Genotyper can perform recalibration only for reads covering genomic loci that potentially contain SNP/indel. In some embodiments, this step can be multi-threaded to expedite the process.

Optimizations to Alignment Algorithms

Optimizations may also be made to alignment algorithms. In some cases, optimizations to alignment algorithms may be made by optimizing code and/or execution of code. For example, the reuse of objects and memory may help eliminate overhead of memory allocation/deallocation for dynamically allocated objects during multiple iterations of innermost code loops. Pre-allocating buffers and reusing them without further allocation may also optimize an alignment algorithm. In some cases, libtcmalloc may be used for pre-allocation. Moreover, keeping the innermost loops in code simple (e.g., reducing the number of branches as well as instructions) may also help optimize code. Furthermore, using data structures with low overhead may help optimize an alignment algorithm. Additionally, parallelization strategies may also help optimize an alignment algorithm.

With respect to a string comparison, the Needleman-Wunsch, and Smith-Waterman alignment algorithms, SIMD instructions may be used to compare a single string against multiple strings to amortize the cost of reading the first string. In general, SMID strategies may include operation on vectors instead of scalars. The use of vectors may be beneficial in cutting down instruction count. Some processors used in a platform may have special instructions for comparing two strings of length of up to 16 characters (128 bits) at a time using just one instruction. These instructions may be used to cut down the number of branches in the code as well as reduce the instruction count. In some cases, exploiting parallelism at the data level and in the computation may be also beneficial in an optimization utilizing SIMD instructions.

Figure 30:
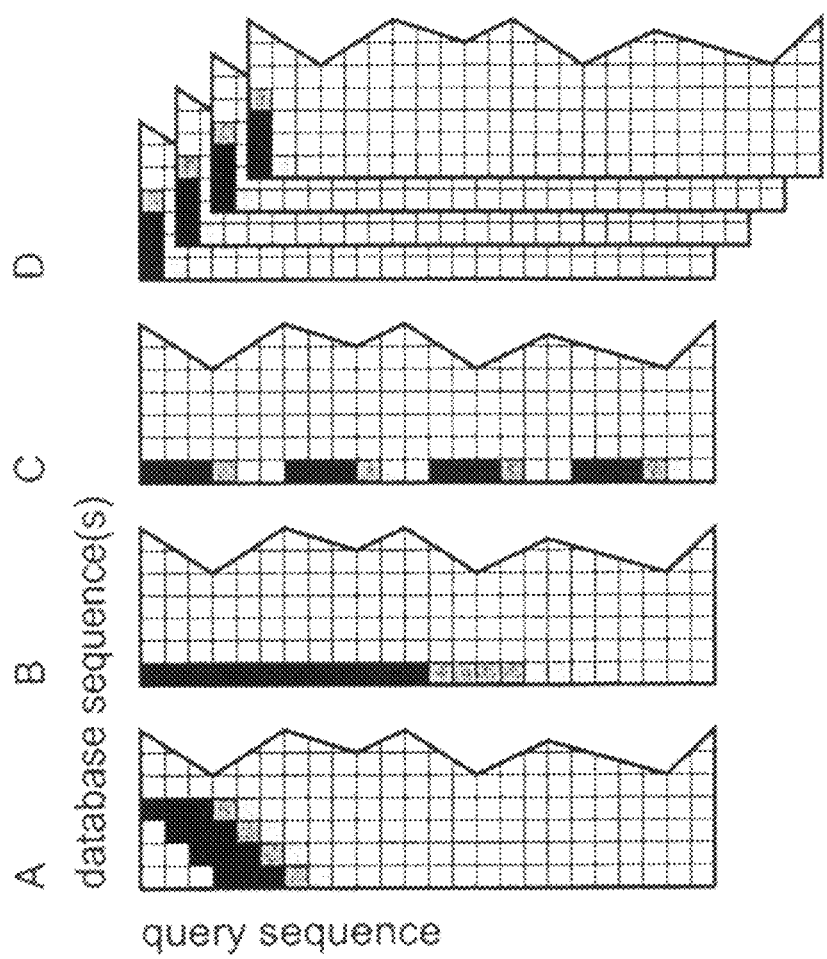
FIG. 30 shows schematic examples of parallelization techniques that may be used with Smith-Waterman and Needleman-Wunsch alignment algorithms.

In cases where Needleman-Wunsch and Smith-Waterman are implemented without backtrace, exploitation of anti-diagonal parallelism in an alignment job may improve the efficiency of an alignment algorithm in cases where the number of reference reads is small. In cases where the number of reference reads is large, exploiting parallelism among alignment jobs may be used to improve the efficiency of an alignment algorithm. Example parallelism techniques (e.g., see Rognes, BMC BIOINFORMATICS, 2011; 12:221, which is entirely incorporated herein by reference) are shown in FIG. 30. Cells of the same color are computed in parallel. Technique A and D may be implemented in an aligner. Technique A may also be implemented on an FPGA. In one example, technique D resulted in a 2.5× improvement in speed over techniques A, B, and C as it comprises a relatively compact inner loop compared to the others.

Additional optimizations may be made to a Needleman-Wunsch alignment algorithm. In some cases, pre-computing a read profile may help optimize a method. For example, assuming that allowed characters are 0, 1, 2, 3, pre-computation of a vector comprising match/mismatch scores for all possible read character values may be achieved. A mismatch score may then be obtained via a table lookup.

In some cases, a Needleman-Wunsch alignment algorithm may be optimized by utilizing row register blocking, wherein the use of registers to keep scores for some rows in a column reduces the number of loads and stores needed to load and store scores.

In some cases, a Needleman-Wunsch alignment algorithm may be optimized by utilizing loop unrolling techniques. Moreover, splitting a Needleman-Wunsch alignment algorithm may optimize the algorithm if a large enough section of matches is present. In this case, alignment of left and right subparts may commence. In one example, splitting a Needleman-Wunsch alignment algorithm resulted in 2× improvement in performance, wherein less than half of a scoring table was computed.

In some cases, a Needleman-Wunsch alignment algorithm may be optimized by utilizing a Python-based code generator. The use of a Python-based code generator may aid in enabling easy exploration of an optimization space.

Other Code Optimizations

In some cases, optimizations may be made to a set insert object.—In general, a set object may be used to keep track of locations which have already been aligned against to avoid doing the same computation again. In one example, the only available operations to this set object were an inserting location operation and a set clearing operation. In some cases, a set data structure may be optimized to have a constant time (O(1)) insertion operation. Such optimization may be completed by using a hash table. In some examples, a small hash table may be sufficient if the maximum number of entries in the set object is small. A small hash table may, thus, be beneficial as it may enable cache reuse and may reduce the cost of accessing a set object. In one example, 5× improvements in the performance of the set insert operation were achieved by utilizing a hash table. A further speedup of 2× was achieved using a small hash table.

The Standard Template Library (STL) lower_bound and upper_bound functions may be used to find hash table entries corresponding to a given kmer—upper_bound may be used to obtain the start index and lower_bound may be used to obtain the ending index into a hash table. Optimization to this process may be achieved by replacing the lower_bound and upper_bound functions with functions configured for the specific data type for a kmer dictionary (the dictionary may be stored as a hash table using part of the kmer as an index into the hash table). Moreover, unlike the case of lower_bound and upper_bound functions that incur an overhead of a function call for comparing characters, an optimized function may also eliminate such a function call overhead.

Use of Optimized Hardware Configurations and Associated Techniques

Figure 25:
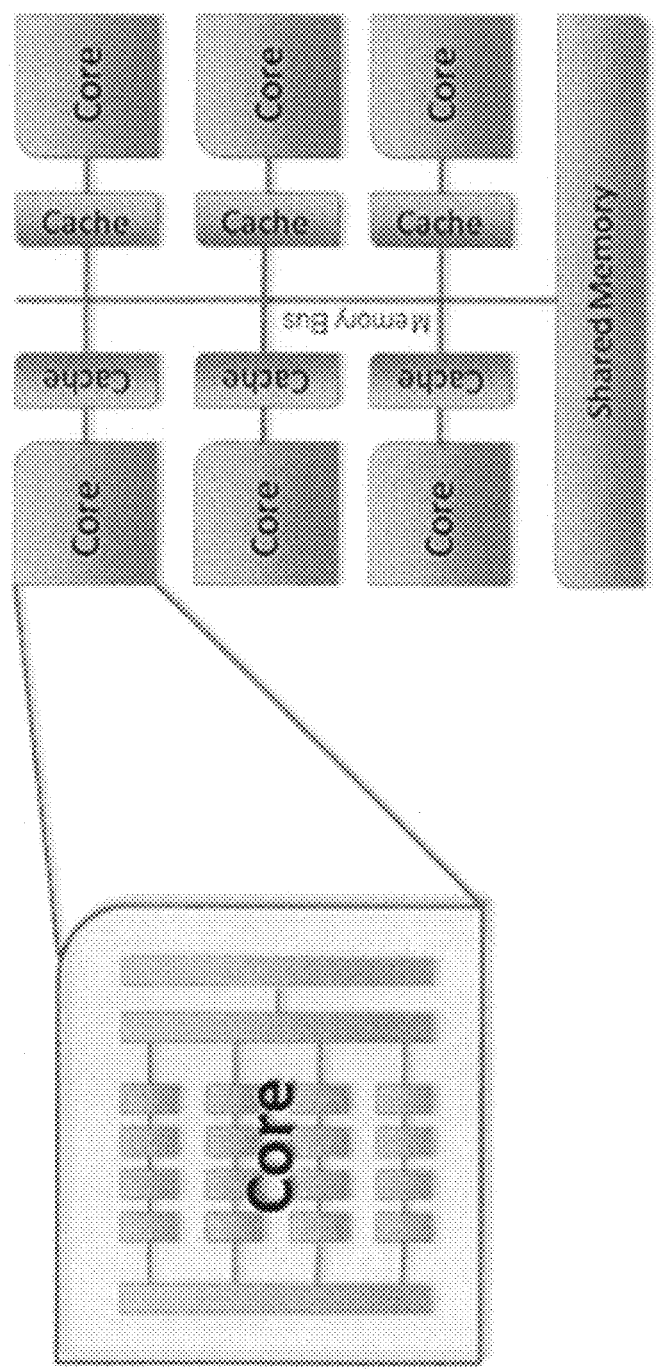
FIG. 25 shows an example parallel processor comprised of multiple cores and shared memory.

In some cases, it may be beneficial to utilize particular hardware configurations. For example, techniques implemented by highly parallel processors with multiple cores on a chip and vector instruction set may be used to reduce times required to perform the Smith-Waterman and Needleman-Wunsch alignment algorithms. An example of highly-parallel processors with multiple cores and shared memory is shown in FIG. 25. Non-limiting examples of such techniques that may be used to accelerate either the Smith-Waterman and/or Needleman-Wunsch alignment algorithms include distributing multiple reads to multiple cores to be processed concurrently, packing multiple reference sequences into one vectorized sequence, and on-the-fly repacking of read sequences for vectorized execution. These techniques may be implemented on both CPU and GPU based platforms.

Figure 26:
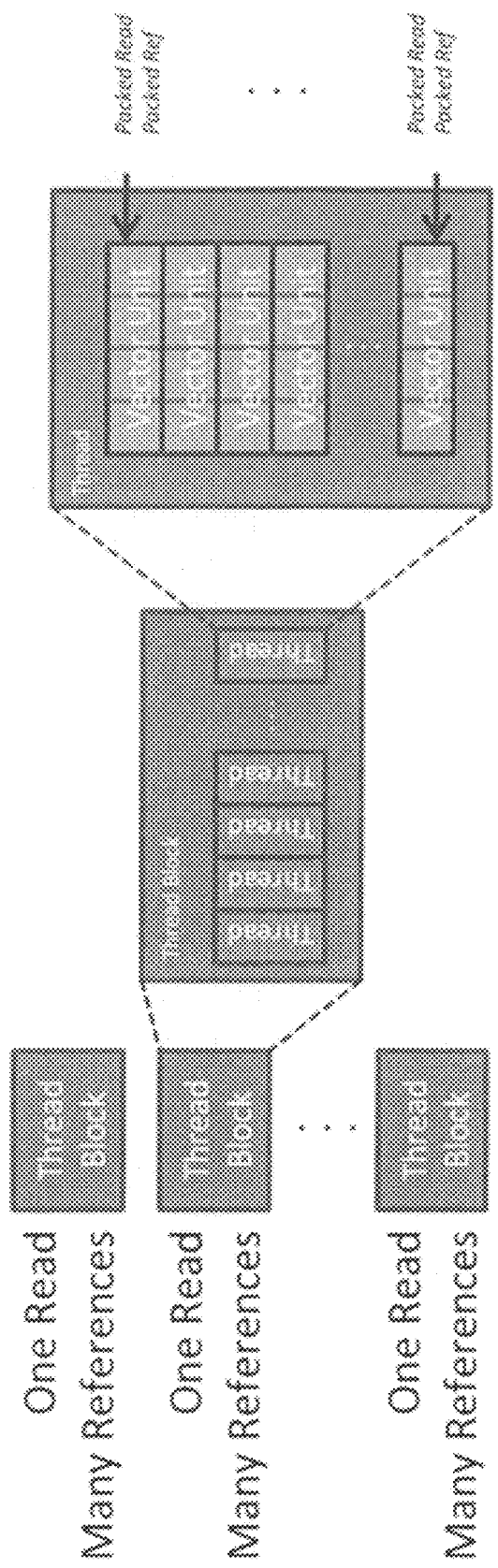
FIG. 26 shows an example distribution of workload to thread blocks.

The first technique, distributing multiple reads to multiple cores to be processed concurrently, may be used to accelerate Smith-Waterman and Needleman-Wunsch algorithms by focusing on the alignment of one read sequence with respect to multiple reference sequences at a time. A group of threads that are mapped to the same core (a "thread block") may be used to parallelize the alignment process. In one example, the input of one thread block may be one read sequence, and a set of an average of 100 reference sequences. The output may be the sequence with the best alignment score. The read sequence may be cached and reused, and all threads may follow a regular computation and memory access pattern that allows platform resources to be maximally utilized. An example of this technique is provided in FIG. 26, where one read and many references are mapped to a thread block, which contains many threads, each of which processes a subset of the reference sequences.

The second technique, packing multiple reference sequences into one vectorized sequence, may be used to accelerate Smith-Waterman and Needleman-Wunsch algorithms by taking advantage of vector instructions present in a multiple-core system. By packing multiple reference sequence into a vector and using vector instructions, each thread can be used to align one read sequence with multiple reference sequences at the same time.

Figure 27:
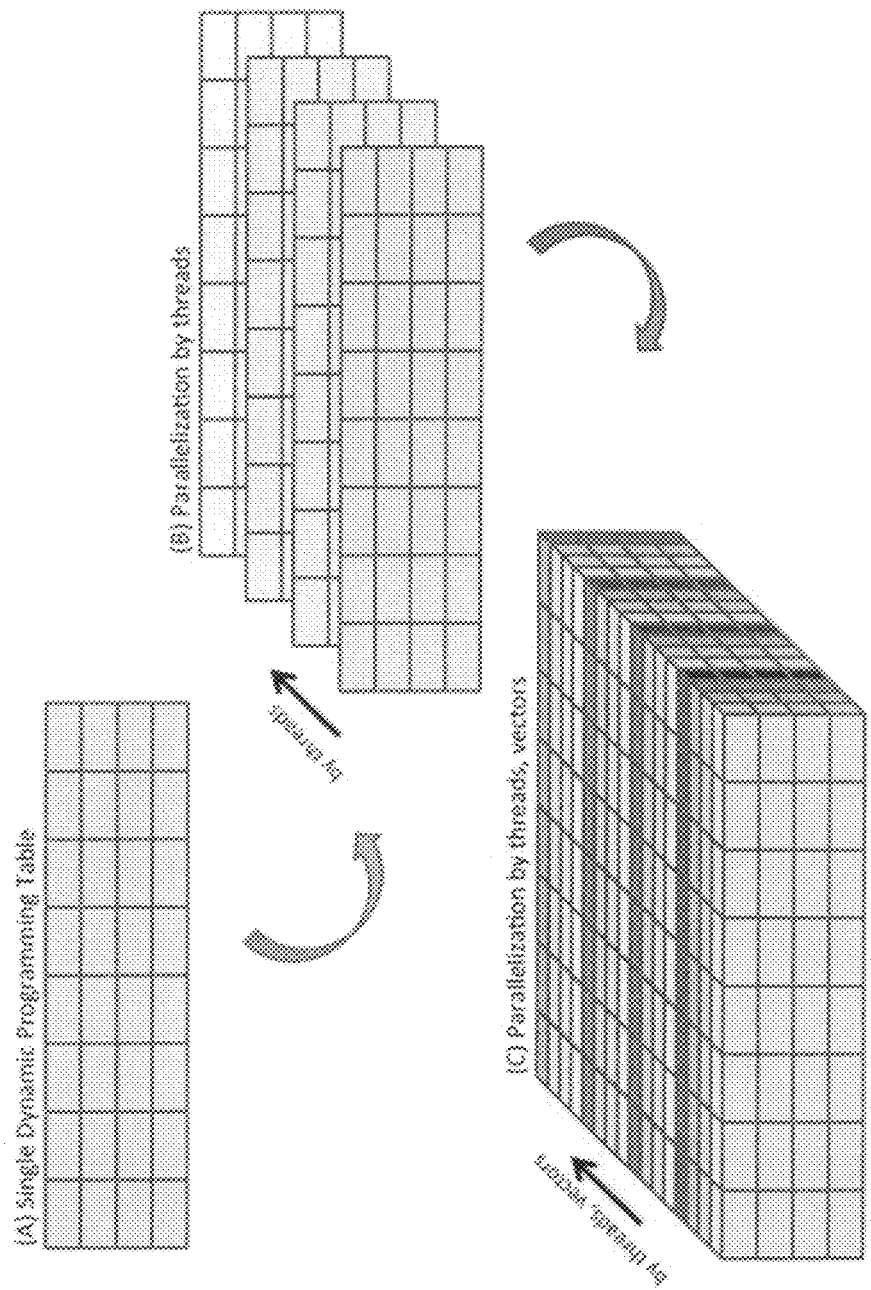
FIG. 27 shows an example of thread block level parallelization.

The alignment of one read sequence with one reference sequence may be included in a typical dynamic programming kernel (FIG. 27A). For efficiency, processing of one read sequence with multiple reference sequences with multiple threads on a GPU may involve careful repacking of the reference sequences (FIG. 27B).

Figure 28:
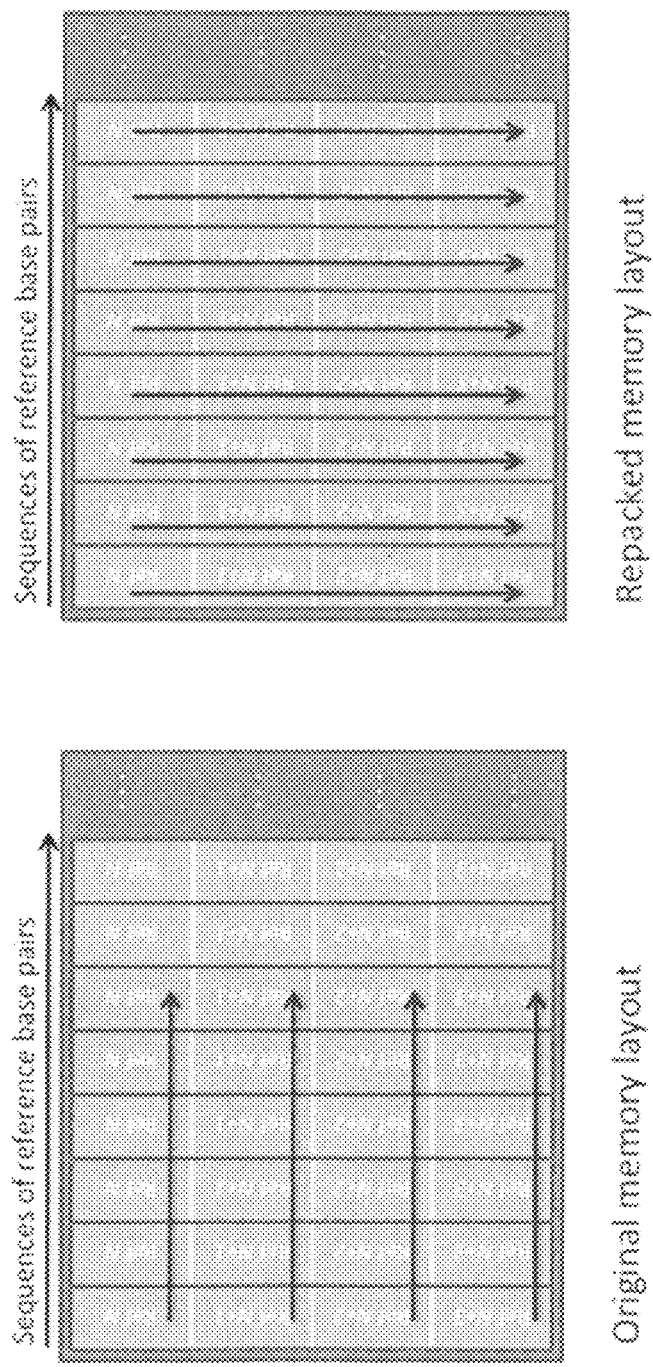
FIG. 28 shows an example of reference sequence memory reordering.

Reference sequences may be stored in memory with each sequence storing its own consecutive base pairs. To efficiently process the alignment of one read sequence with multiple reference sequences, the memory layout may be rearranged to a new order, as shown in FIG. 28. Such a packing process may be a one-time cost for the alignment of a read sequence to its set of reference sequences, and the benefit of the new memory layout may be realized for the computation of each row of the dynamic programming table.

Using vector instructions, reference sequences may be further packed in the new memory layout into a vectorized reference sequence, where four sequences of the reference base pairs are packed into the same array integers. In one example, four sequences of the reference base pairs are packed into the same array of 32-bit integers. Vectorized compaction may result in a significant savings with respect to the a caching infrastructure and may generally improve the effective capacity of the memory subsystem.

The third technique, on-the-fly repacking of read sequences for vectorized execution, may be used to accelerate Smith-Waterman and Needleman-Wunsch algorithms, by repacking read sequences into a vector that may be used with vector instructions. The read sequence is a sequence of base pairs with four possible manifestation (A,C,T,G) that can be represented in 2 bits. Read sequences may be stored as packed words. In one example, a packed word contains up to 16 base pairs in a 32-bit integer.

Figure 29:
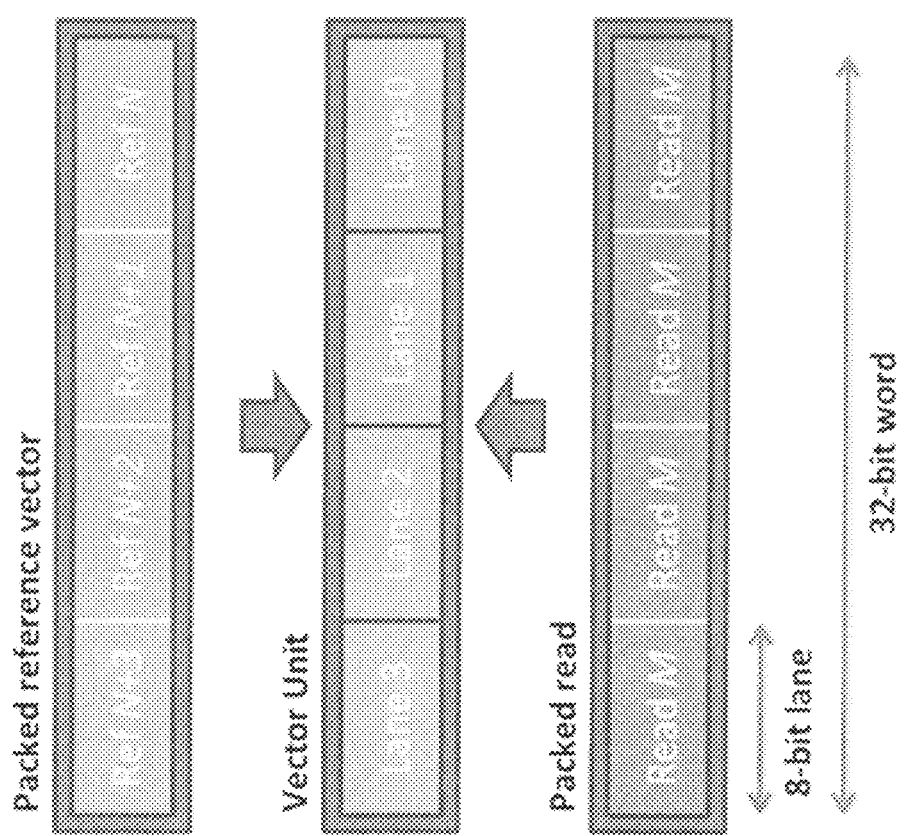
FIG. 29 shows an example of a read sequence repacking pattern.

Using vector instructions, read sequences may be repacked to match the packing pattern of the reference sequences at run time. FIG. 29 illustrates an example packing pattern within a 32-bit operation.

As the reference vector is packed with base pairs from different reference sequences, the read vector may be packed with base pairs from the same position in the read sequence. This packing pattern may allow a cell update procedure to take place with the maximal amount of vector instructions.

EXAMPLES

Example 1

SeqAlto Alignment

Mu et al., BIOINFORMATICS, 2012; 28(18):2366-73, which is entirely incorporated herein by reference, provides a sequence alignment platform and its comparison to existing platforms. Additional information on command parameters, single-end reads, variant calling, error rates, and correctness criteria used for the platform is also provided.

Example 2

Comparison of Exemplary Hardware/Software Integrated Platforms

Different versions of the Needleman-Wunsch Aligner are tested after integration into the various hardware platforms, as set forth below.

Table 1 shows results using the Affine variant of the Needleman-Wunsch Aligner after integration into various platforms (CPU, FPGA, GPU), demonstrating that FPGA Bound results in greater speed performance.

TABLE 1

CPU, FPGA and GPU results.

|  | CPU 16-bit SIMD | CPU 8-bit SIMD | FPGA Bound | FPGA Achieved | GPU Bound | GPU Achieved |
|---|---|---|---|---|---|---|
| align/sec | .9M | 1.8M | 9.6M | 2.2M | 1.M | .6M |
| GCUP/s | 29 | 58 | 314 | 72 | 40 | 20 |

The Affine, Standard, and Area-Optimized versions of the Needleman-Wunsch Aligner are tested after integration into FPGA Achieved or Bound platforms. Table 2 depicts results comparing different versions of the Needleman-Wunsch Aligner after integration into the FPGA platforms, demonstrating that the Area-Optimized version of the aligner integrated with the FPGA-Bound platform greatly increases the alignment speed.

TABLE 2

Needleman-Wunsch Aligner results.

|  | Affine | | Standard | | Area-Optimized | |
|---|---|---|---|---|---|---|
|  | align/sec | GCUP/s | align/sec | GCUP/s | align/sec | GCUP/s |
| Achieved | 2.2M | 72 | 4.2M | 144 | 12M | 393 |
| Bound | 9.6M | 314 | 14M | 458 | 48.1M | 1573 |

TABLE 3

NW Variants on FPGA ("CUP" = cell updates)

| (1) | (2) Affine | | (3) Standard | | (4) Area-Optimized | |
|---|---|---|---|---|---|---|
|  | (5) lign/sec | (6) CUP/s | (7) lign/sec | (8) CUP/s | (9) lign/sec | (10) CUP/s |
| (11) chieved | (12) .2M | (13) 2 | (14) .2M | (15) 44 | (16) 2M | (17) 93 |
| (18) ound | (19) .6M | (20) 14 | (21) 4M | (22) 58 | (23) 8.1M | (24) 573 |
| (25) | (26) | (27) | (28) | (29) | (30) | (31) |

Example 3

Comparison of Aligners

Figure 16:
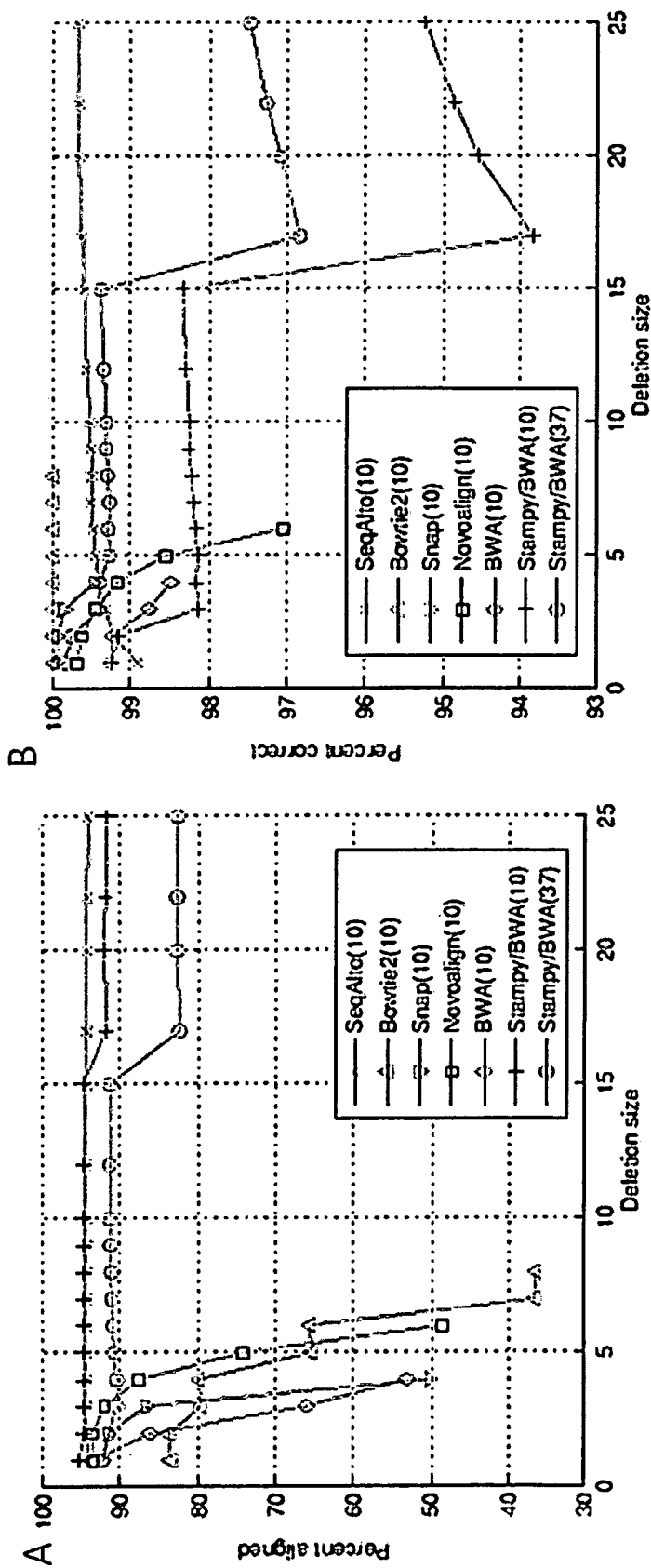
FIG. 16 shows a comparison of alignment accuracy between a platform of the invention and other available platforms as a function of deletion size.
Figure 17:
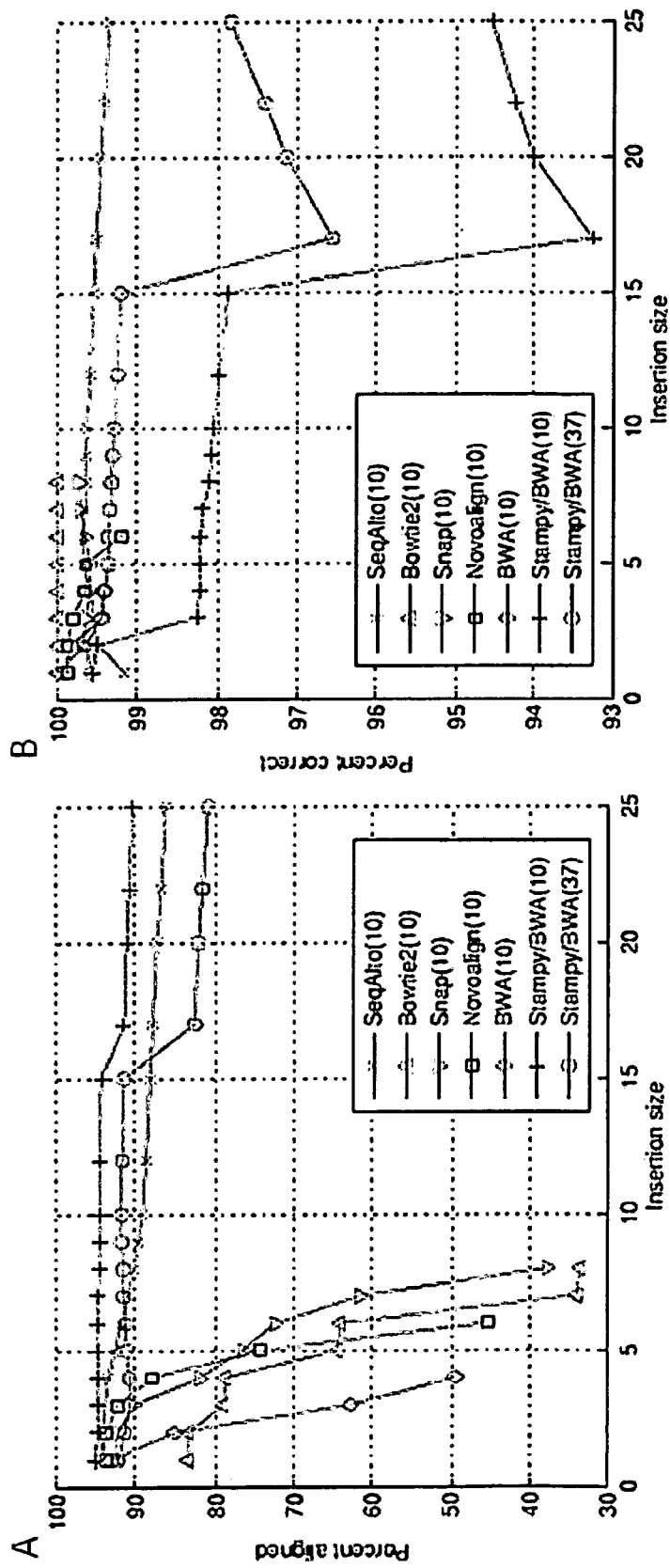
FIG. 17 shows a comparison of alignment accuracy between a platform of the invention and other available platforms as a function of insertion size.

FIGS. 16 and 17 show plots of percent aligned (left, A) and percent correct (right, B) taken against deletion size (x-axis) calculated using SeqAlto and other available aligners.

Example 4

Comparison of Aligners

Figure 18:
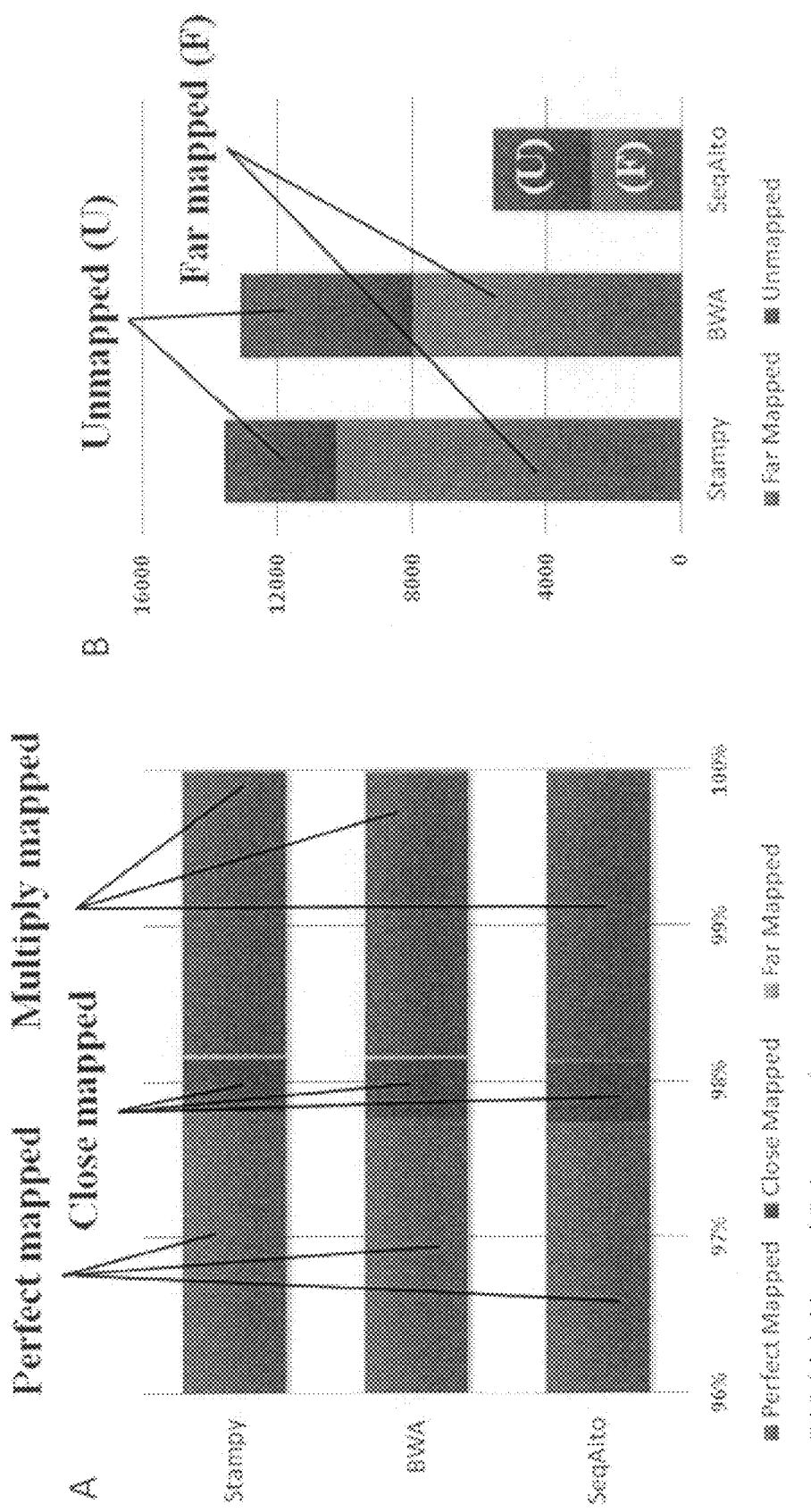
FIG. 18 shows a comparison of alignment accuracy between a platform of the invention (SeqAlto) and other available platforms (Stampy and BWA). A comparison, for each read, between the output of the aligner and true (golden) alignment is shown.

FIG. 18 shows a comparison of alignment accuracy between SeqAlto and other available aligners (Stampy and BWA). A comparison, for each read, between the output of the aligner and true (golden) alignment is shown.

Example 5

Comparison of Aligners

Figure 19:
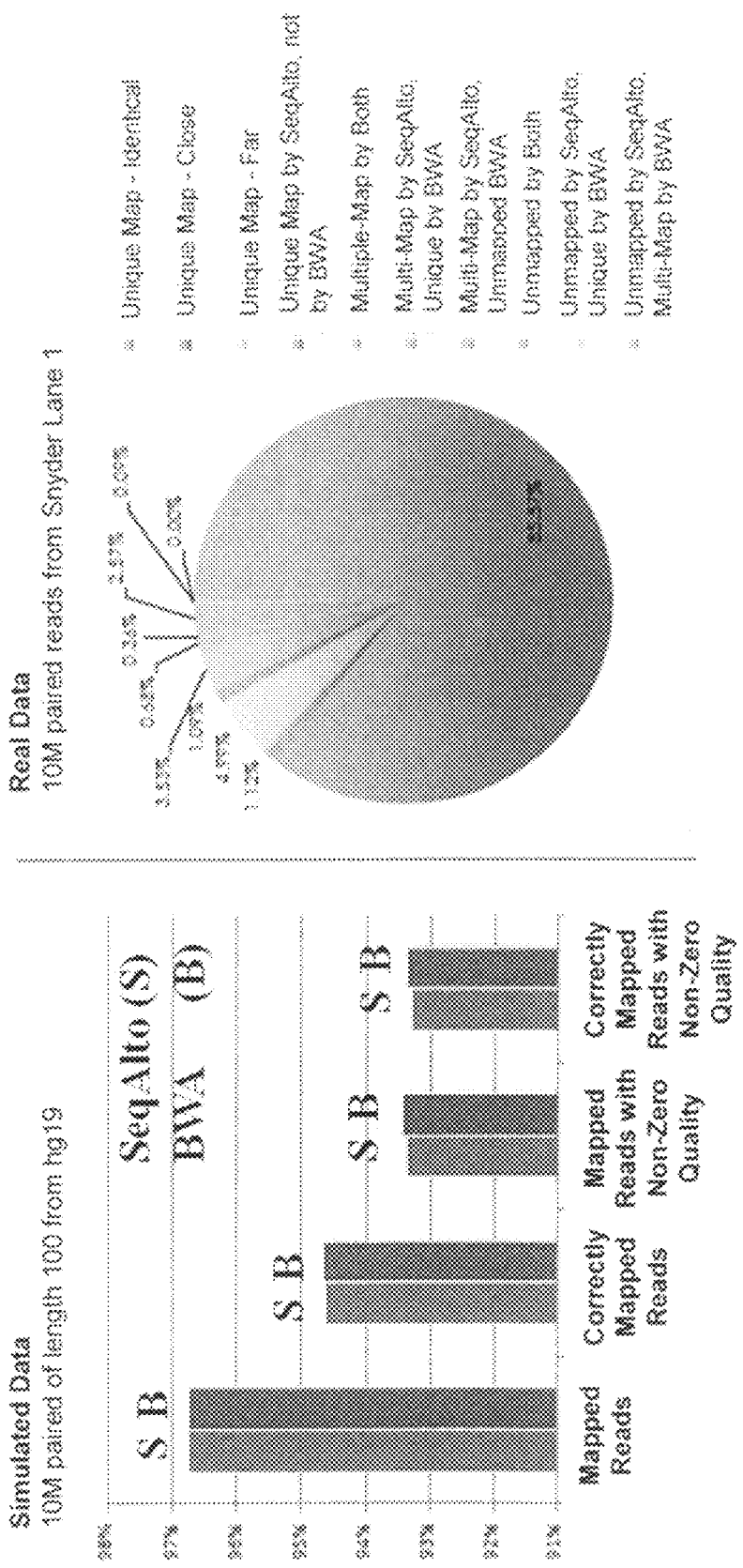
FIG. 19 compares the SeqAlto aligner (left vertical bars) with a BWA aligner (right vertical bars), showing simulated data (left) and real data (right).

FIG. 19 compares the SeqAlto aligner with a BWA aligner, showing simulated data (left) and real data (right). This plot shows the improved performance of the SeqAlto aligner of the present disclosure in relation to other aligners. With respect to results regarding the real data, 85.57% of the reads were unique maps and identical between the two alignment methods as shown in the pie chart. The remaining 14.43% corresponded to a mix of different results between the two methods.

Example 6

Comparison of Aligners

Figure 20:
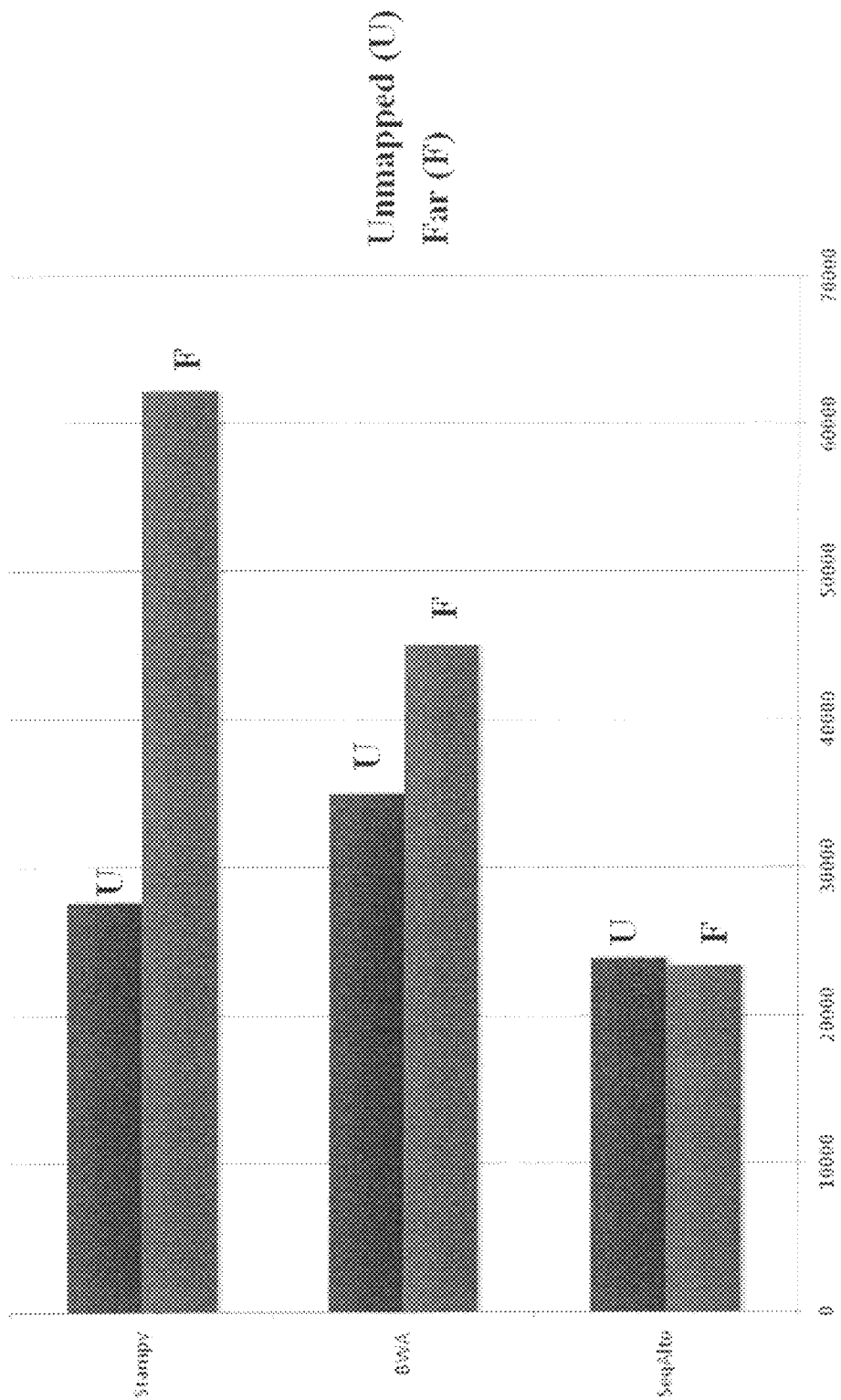
FIG. 20 shows the alignment accuracy (unmapped (top horizontal bars) and far mapped (bottom horizontal bars)) for an aligner of the invention (SeqAlto), the BWA aligner and the Stampy aligner.

FIG. 20 is a bar plot showing the alignment accuracy (unmapped and far mapped) for SeqAlto, the BWA aligner and the Stampy aligner. The SeqAlto aligner has fewer unmapped and far mapped reads.

Example 7

Comparison of Aligners in Combination with Variant Calling Tools

Figure 21:
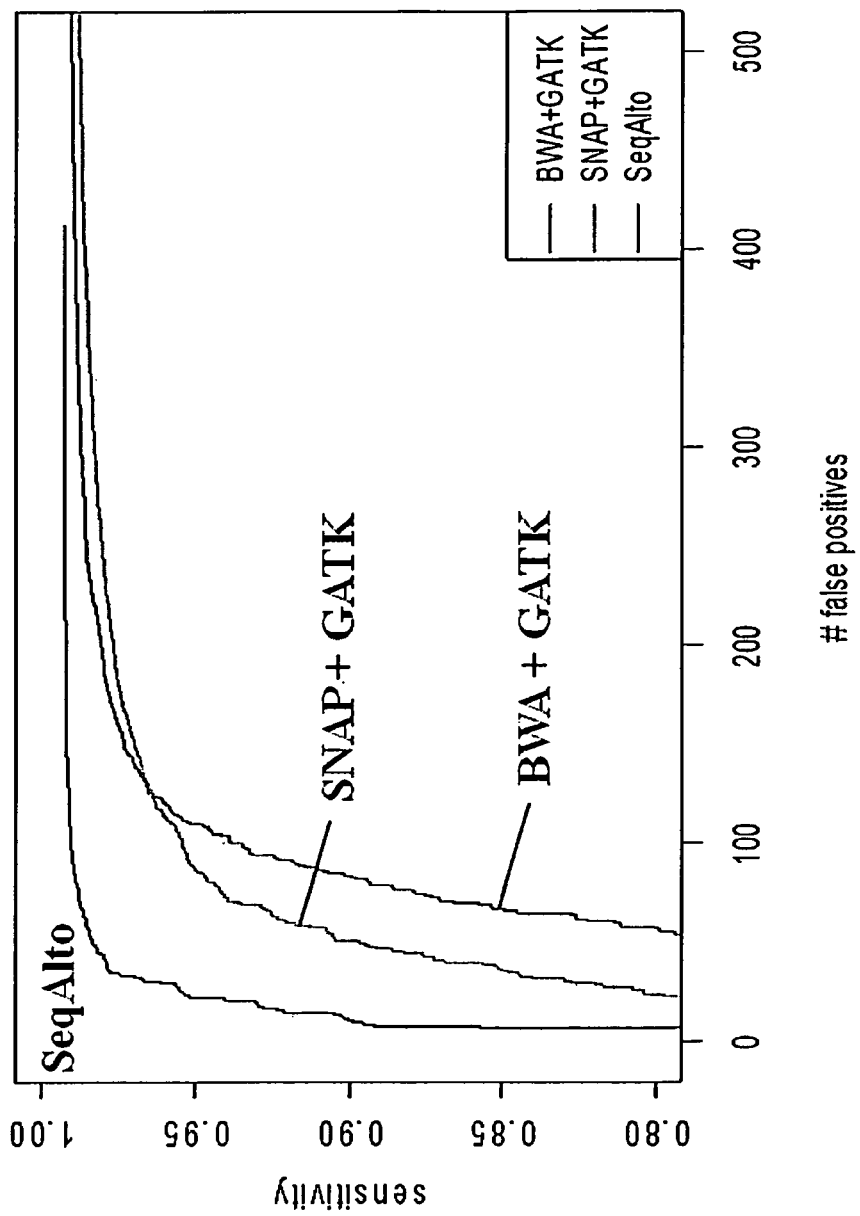
FIG. 21 is a plot showing sensitivity against the number of false positives for the SeqAlto platform, SNAP+GATK platform, and BWA+GATK platform.
Figure 22:
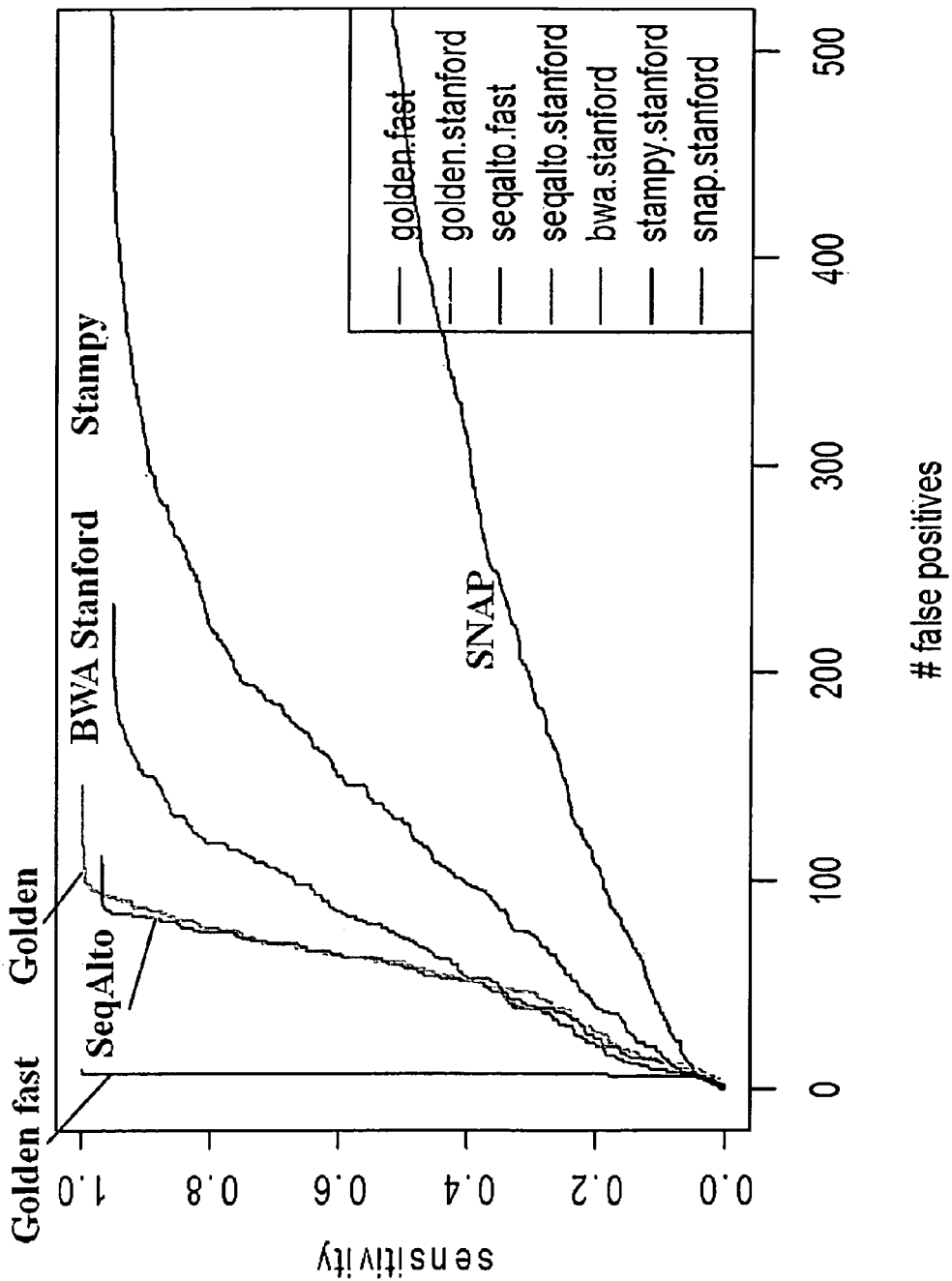
FIG. 22 is a plot showing sensitivity against the number of false positives for the SeqAlto platform and various other platforms.

FIG. 21 is a plot showing sensitivity against the number of false positives for the SeqAlto aligner, SNAP+GATK platform, and BWA+GATK platform. FIG. 22 is a plot showing sensitivity against the number of false positives for the SeqAlto aligner and various other platforms.

Example 8

Variant Calling

Figure 23:
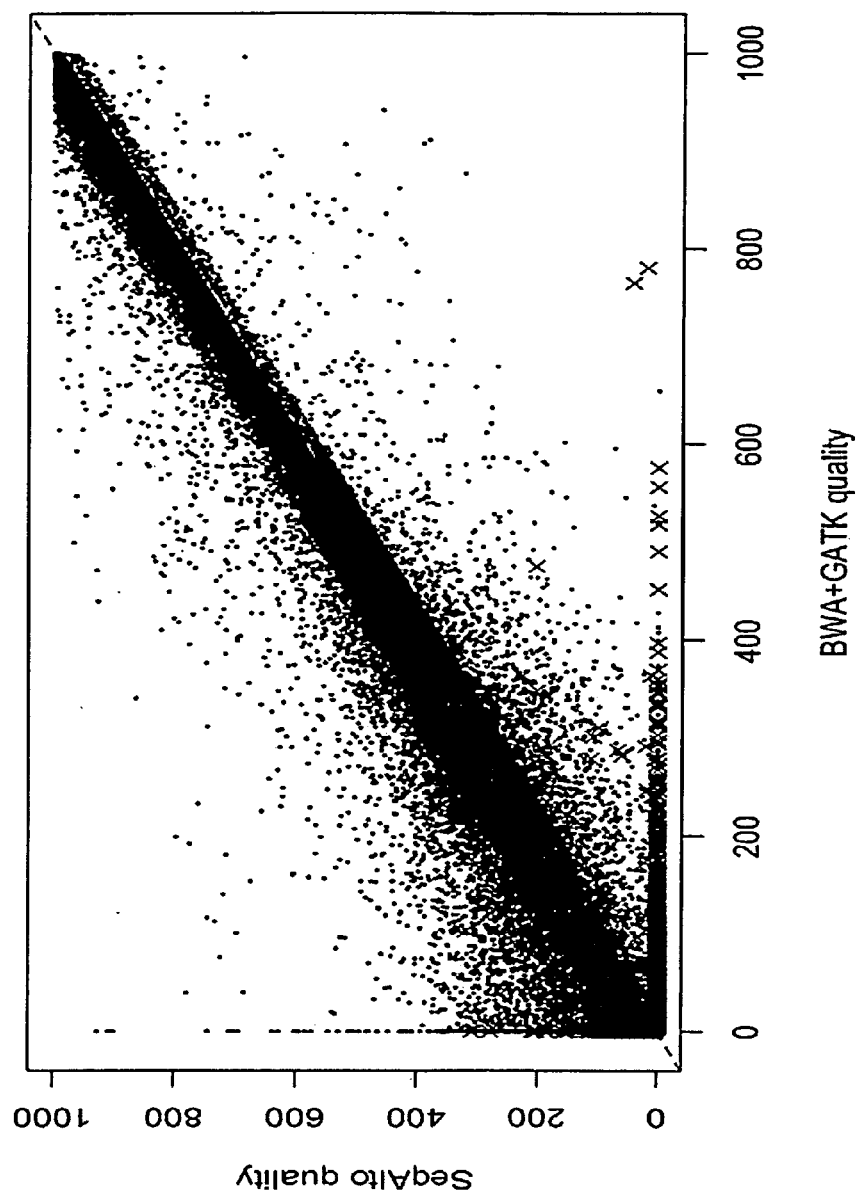
FIG. 23 shows different variations in the genome that is called by an aligner of the invention (y-axis) and other aligners (BWA+GATK, x-axis). The dots show real data, and the X's show inaccuracies. Fewer X's correspond to improved performance.

FIG. 23 shows variations in the genome that is called by an after alignment with SeqAlto (y-axis) and other aligners (BWA+GATK, x-axis). The dots show real data, and the X's show inaccuracies. Fewer X's correspond to improved aligner performance.

Example 9

Variant Calling with Modular Platform

Indels and SNPs are called using a 5 node platform, similar to the example platform described in FIG. 24. Indels and SNPs are called for Snyder genomic sequence data with 40× coverage in about 4 hours.

Example 10

SamSorter

An example operation of SamSorter is provided. First, Sam-Sorter receives as input a SAM file and a BED file. A SAM file may be read from a file or a pipe and includes aligned reads in SAM format. A BED file may include the genomic region and/or the overall range in which the reads are being sorted. A number N (the number of output files) is specified to create N parallel threads for the downstream tools. In addition, the maximum amount of memory to use for storing records+sorting table is specified. SamSorter is executed.

SamSorter splits the output file into N output BAM files with corresponding BED interval files. Output may also include a coordinate-sorted, duplicate removed (or marked), BAM file for each region in the supplied BED file; a depth-of-coverage folder containing coverage levels for each region in the supplied BED file; and/or a ui-coverage folder containing coverage levels for various window sizes.

Example 11

In-Memory Sorting; SamTools

An example of in-memory sorting is provided as it may be used in an example implementation in SamSorter.

First, a stream is checked for emptiness. If the stream is empty, in-memory sorting completes. Otherwise, two records from the stream are read (e.g., two ends of a paired read). A duplicate position is then calculated. To calculate a duplicate position for mapping to a forward strand, all hard and soft clippings indicated by a CIGAR string from the mapping position are subtracted. To calculate a duplicate position for mapping to a negative strand, all matches and deletions to the mapping position are added to obtain the end of the alignment on a reference. Backward iteration through the CIGAR string then may add soft and hard clips to the position calculated.

Next, mate duplicate positions and scores between the two records are exchanged. Memory is checked to see if memory exists for storing records. If no memory is available, the records to be stored are written to a disk. The records are then inserted at duplicate positions and the algorithm repeats until the stream is empty.

In some cases (for pairs; single-end data is also handled), the 5' coordinates are fund and orientations of each read pair are mapped. This approach may take into account all clipping as well as any gaps or jumps in the alignment. This can include the determination as to whether all of the bases from a read are aligned, and if so, where the alignment would have occurred. All read pairs that have identical 5' coordinates and orientations can then be matched, and all but the "best" pair can be marked as duplicates. "Best" can be defined as the read pair having the highest sum of base qualities as bases with $Q>=15$.

Example 12

SamSorter

The SamSorter is applied for a full human genome dataset of 40× on a one node configuration and compared to Picard Tools. The sorting time is reduced from X to Y, and the overall sort+merge+duplicate removal is reduced from X to Y. Results obtained are shown in Table 4. Results are achieved by leveraging large amount of RAM and minimizing random input/output (I/O) and redundant operations in the pipeline.

TABLE 4

Results of SamSorter Run in Example 12

| | | |
|---|---|---|
| samsorter(sort, rmdup, split) | 3:25 (overlapped, 1:08) | ds5, 31m, WG (data set 5 simulated data, 31 million reads) |
| Picard(SortSam) | 7:29 | ds5, 31m, WG |

TABLE 4-continued

Results of SamSorter Run in Example 12

| Picard(MarkDuplicates) | 6:06 | ds5, 31m, WG |
| --- | --- | --- |
| samsorter(sort, rmdup, split) | 16:36 (overlapped, 3:51) | snyder, 200m, WG, lane 1 (200 million reads, lane 1 and lane 2 are different subsets of the read data set) |
| Picard(SortSam) | 52:35 | snyder, 200m, WG, lane 1 |
| Picard(MarkDuplicates) | 35:45 | snyder, 200m, WG, lane 1 |
| samsorter(sort, rmdup, split) | 16:38 (overlapped, 4:15) | snyder, 200m, WG, lane 2 |
| Picard(SortSam) | 53:28 | snyder, 200m, WG, lane 2 |
| Picard(MarkDuplicates) | 35:54 | snyder, 200m, WG, lane 2 |

Example 13

Optimizing Alignment Algorithms

This example provides an optimization to a string comparison algorithm. A naive implementation of string comparison is coded as follows:

```
for (i = 0, mismatches = 0; i < n; i++) {
    if (a[i] != b[i]) mismatches = mismatches + 1
    if (mismatches > max_mismatches) break
}
```

Two key optimizations (reducing the number of code branches and number of instructions) are performed to the code above. SIMD instructions are used to compare a single string a against multiple strings b to amortize the cost of reading the string a. An Intel processor having special instructions for comparing two strings of length up to 16 characters (128 bits) at a time using just one instruction are utilized. These instructions reduce the number of branches in the code as well as reduce the instruction count. An example of an optimized string comparison pseudo-code is as follows:

```
// a is the string of length n
// b is an array of n_nrefs strings
// pcmpestrm is the Intel instruction to count the number of matches/mismatches
// popcnt instruction counts the number of 1's in a number
for (i = 0; i < n_refs; i += 4) {
    mismatch0 = 0, mismatch1 = 0, mismatch2 = 0, mismatch3 = 0
    for (j = 0; j < n; j = j + 16) {
        load a[j:j+15] into SIMD register a_chars
        load b[i][j:j+15] into SIMD register b_chars_0
        load b[i+1][j:j+15] into SIMD register b_chars_0
        load b[i+2][j:j+15] into SIMD register b_chars_0
        load b[i+3][j:j+15] into SIMD register b_chars_0
        mismatch0 += popcnt (pcmpestrm (a_chars, b_chars_0))
        mismatch1 += popcnt (pcmpestrm (a_chars, b_chars_1))
        mismatch2 += popcnt (pcmpestrm (a_chars, b_chars_2))
        mismatch3 += popcnt (pcmpestrm (a_chars, b_chars_3))
        if (mismatch0 > max_mismatches && mismatch1 >
            max_mismatches && mismatch2 >
            max_mismatches && mismatch3 > max_mismatches)
            break;
    }
    mismatch_count[i  ] = mismatch0;
    mismatch_count[i+1] = mismatch1;
    mismatch_count[i+2] = mismatch2;
    mismatch_count[i+3] = mismatch3;
}
```

The optimized code above results in a reduction in the number of instructions needed to compare the two strings, compare the number of mismatches to maximum number of mismatches, as well as count the number of mismatches. The code optimizations enable a 2× improvement in speed over the naive code.

In addition, the read string a can be stored at an address aligned to 16 bytes to enable using aligned loads in the SIMDized code. The Intel lddqu instruction may be utilized for faster loads from unaligned addresses to SIMD registers. Moreover, the optimized code can unroll the innermost loop if the string length is known. In some cases, an automatically tuned version of string comparison which chooses between different variants of the code depending on the read length and the number of references may provide even further optimization.

Example 14

Optimizing Alignment Algorithms

For codes implementing versions of the Needleman-Wunsch and Smith-Waterman algorithms without backtrace, SIMD implementations of the codes may be used for optimization. As only an optimum score needs to be computed, maintenance of two rows of the score matrix is completed. Such an arrangement allows cache reuse, since a cyclical buffer can be used to store the current and the previous rows of the score matrix. The SIMD implementation may be optimized by removing as many branches as possible from the innermost loop. In some cases, the loops may be split to enable branchless loops. Such code restructuring improves the time efficiency of the SIMD implementations by almost 2×, in addition to the 15× time efficiency obtained by using SIMD versions of the codes.

For the backtrace version of the Needleman-Wunsch and Smith-Waterman codes, non-SIMD implementations of the codes may be used. Loop splitting and unrolling may be used to simplify the most compute intensive innermost loops of the codes. Since the optimum score in the Needleman-Wunsch code may only occur in the last row, a cyclical buffer optimization may be used to reduce the memory footprint of the respective code. Such code optimization may improve the time efficiency of these codes by about 1.5×.

Example 15

Use of Vector Instructions

In an example, an implementation inner loop uses six 64-bit operations, 27 32-bit operations, and 10 packed 8-bit operations, with theoretical peak of 36 GCUPS of performance.

Example 16

Benchmarking Alignment Algorithms

The Needleman-Wunsch (NW) and Smith-Waterman (SW) alignment algorithms are benchmarked. The restrictive NW formulation has more parallelism within a single-cell update compared to the non-restrictive formulation and requires more memory and registers. NW performance scales inversely with bitwidth, such that it is expected that the 8-bit version of NW is expected to get twice the performance of the 16-bit version. The 8-bit version of SW uses saturating arithmetic due to narrow bitwidth, adding extra instructions. Single-threaded, alignment performance (Alignments/s and Giga Cell Update Per Second (GCUPS)) results for different versions of the Needleman-Wunsch and Smith-Waterman are shown in Table 5. Additional benchmarking statistics (run time, reads/s, and operations/s (ops/s)) are provided in Table 6.

TABLE 5

Needleman-Wunsch and Smith-Waterman Benchmarking Results

| Kernel | Alignments/s | GCUPS |
|---|---|---|
| NW (restrictive, 16-bit) | 100K | 3.3 |
| NW (16-bit) | 150K | 4.5 |
| SW (16-bit) | 120K | 3.9 |
| SW (8-bit) | 233K | 7.6 |

TABLE 6

Additional Needleman-Wunsch and Smith-Waterman Benchmarking Results

| Kernel | Time (s) | ops/s | Reads/s |
|---|---|---|---|
| String mismatch (single-ended) | 4.11 (14.7%) | 128M | 487K |
| NW (16-bit, single-ended, no backtrace) | 2.68 (9.6%) | 3.9M | 30K |
| NW (16-bit, single-ended, backtrace) | 5.74 (20.1%) | 67.7K | 14K |
| String mismatch (paired) | .98 (3.5%) | | |
| SW (8-bit, pairing, no backtrace) | 1.67 (5.9%) | | 1.35M |
| NW (16-bit, pairing, backtrace) | 1.18 (4.2%) | 67.7K | |
| SW (16-bit, pairing, backtrace) | .44 (1.6%) | 50K | |
| Set insert (single-ended) | 1.3 (4.6%) | | 455M |
| Concordant pairs gen (paired) | 1.35 (4.8%) | | |
| Output gen | .42 (1.5%) | | |
| Read | .44 (1.6%) | | 4.5M |
| Overall | 28 (100%) | | 71K |

It should be understood from the foregoing that, while particular implementations have been illustrated and described, various modifications can be made thereto and are contemplated herein. It is also not intended that the invention be limited by the specific examples provided within the specification. While the invention has been described with reference to the aforementioned specification, the descriptions and illustrations of the preferable embodiments herein are not meant to be construed in a limiting sense. Furthermore, it shall be understood that all aspects of the invention are not limited to the specific depictions, configurations or relative proportions set forth herein which depend upon a variety of conditions and variables. Various modifications in form and detail of the embodiments of the invention will be apparent to a person skilled in the art. It is therefore contemplated that the invention shall also cover any such modifications, variations and equivalents. It is intended that the following claims define the scope of the invention and that methods and structures within the scope of these claims and their equivalents be covered thereby.

What is claimed is:

1. A system for processing genetic sequence data from a genomic sequencing device, the system comprising:
   an input for receiving the genetic sequence data from a sequencing of a sample from a human subject by the genomic sequencing device;
   a plurality of nodes connected to each other, each node comprising:
      a computer server including one or more processors;
      a programmable logic device having an alignment engine that is programmed to perform alignment of the genetic sequence data to reference sequences retrieved by a memory controller from a first memory, thereby obtaining aligned genetic sequence data;
      a communication bus between the computer server and the programmable logic device for transferring sequence reads of the genetic sequence data from the computer server to the alignment engine and for transferring instructions to the memory controller configured to retrieve the reference sequences from the first memory; and
   network connections to other nodes for transferring aligned reads identified by an alignment demultiplexer, wherein the alignment demultiplexer is configured to identify which node is responsible for a genomic region corresponding to an aligned read,
   wherein the computer server is configured to:
      sort, based on location, aligned reads generated by the node and received from other nodes, thereby obtaining a sorted list of aligned reads,
      split the sorted list into N sorted regions, and
      perform a multi-threaded execution of a variant analysis and a structural variant analysis on the aligned reads of the N sorted regions, each thread operating on aligned reads of one of the N sorted regions;
   wherein the computer servers are configured to perform the variant analysis and the structural variant analysis on said aligned genetic sequence data having at least about thirty times coverage of a human genome, wherein the alignment, variant analysis, and the structural analysis is performed in a time period less than or equal to about 4 hours.

2. The system of claim 1, further comprising a memory location with machine-executable code that programs said programmable logic device to implement the alignment of said genetic sequence data to provide the aligned genetic sequence data.

3. The system of claim 1, wherein said programmable logic device is programmed to perform alignment on said genetic sequence data with at least about 95% accuracy as measured by a percentage of mapped reads.

4. The system of claim 1, wherein said programmable logic device is programmed to perform at least about 200,000 alignments per second on said genetic sequence data with at least about 95% accuracy as measured by a percentage of mapped reads.

5. The system of claim 4, wherein said programmable logic device is programmed to perform at least about 200,000 alignments per second on said genetic sequence data with at least about 99% accuracy.

6. The system of claim 1, wherein said time period is less than or equal to about 3 hours.

7. The system of claim 1, wherein said time period is less than or equal to about 1 hour.

8. The system of claim 1, wherein said programmable logic device is a field programmable gate array.

9. The system of claim 1, wherein said programmable logic device is programmed to perform between about 200,000 and 12 million alignments per second.

10. The system of claim 1, wherein the one or more processors of the computer server comprise an in-memory genome region sorter that is programmed to sort said aligned reads.

11. The system of claim 10, wherein the in-memory genome region sorter is configured to output N files corresponding to the N sorted regions.

12. The system of claim 1, wherein the computer server is configured to store the aligned reads in a second memory while sorting the aligned reads.

13. The system of claim 12, wherein the aligned reads are stored in a linked list in the second memory during the sorting of the aligned reads.

14. The system of claim 12, wherein the aligned reads of the N sorted regions are written to a local disk for use in performing the variant analysis and the structural variant analysis.

15. The system of claim 1, wherein the plurality of nodes includes a leader node, and wherein the computer server of the leader node is configured to:
read the genetic sequence data from a storage disk; and
distribute the genetic sequence data among the plurality of nodes so as to balance a load on the plurality of nodes.

16. The system of claim 15, wherein the computer server of the leader node is further configured to:
partition a reference genome among the plurality of nodes, wherein the genetic sequence data is distributed among the plurality of nodes based on partitions assigned to the plurality of nodes.

17. The system of claim 15, wherein the computer server of the leader node is further configured to compile results of the variant analysis and the structural variant analysis from the plurality of nodes.

18. The system of claim 1, further comprising:
the genomic sequencing device.

19. A system for processing genetic sequence data from a genomic sequencing device, the system comprising:
an input for receiving the genetic sequence data from a sequencing of a sample from a human subject by the genomic sequencing device;
a plurality of nodes connected to each other, each node comprising:
a computer server including one or more processors;
a programmable logic device having an alignment engine that is programmed to perform alignment of the genetic sequence data to reference sequences retrieved by a memory controller from a first memory, thereby obtaining aligned genetic sequence data;
a communication bus between the computer server and the programmable logic device for transferring sequence reads of the genetic sequence data from the computer server to the alignment engine and for transferring instructions to the memory controller configured to retrieve the reference sequences from the first memory; and
network connections to other nodes for transferring aligned reads identified by an alignment demultiplexer, wherein the alignment demultiplexer is configured to identify which node is responsible for a genomic region corresponding to an aligned read,
wherein the computer server is configured to:
sort, based on location, aligned reads generated by the node and received from the other nodes, thereby obtaining a sorted list of aligned reads, and
perform a variant analysis using the sorted list of aligned reads.

20. The system of claim 19, wherein the computer server is further configured to:
split the sorted list into N sorted regions, and
perform a multi-threaded execution of the variant analysis on the aligned reads of the N sorted regions, each thread operating on aligned reads of one of the N sorted regions.

21. The system of claim 19, wherein the variant analysis includes a structural variant analysis.

22. A method for processing genetic sequence data from a genomic sequencing device, the method comprising:
receiving, at an input of a computer system, the genetic sequence data from a sequencing of a sample from a human subject by the genomic sequencing device, the computer system comprising a plurality of nodes connected to each other, each node comprising a computer server including one or more processors and a programmable logic device having an alignment engine;
at each node of the plurality of nodes:
using a communication bus between the computer server and the programmable logic device to transfer sequence reads of the genetic sequence data from the computer server to the alignment engine and to transfer instructions to a memory controller configured to retrieve reference sequences from a first memory;
performing, by the alignment engine, an alignment of the sequence reads to the reference sequences retrieved by the memory controller from the first memory, thereby obtaining aligned reads;
identifying, by an alignment demultiplexer, which genomic regions are assigned to which nodes; and
transferring, via network connections to other nodes, aligned reads corresponding to genomic regions of the other nodes,
sort, based on location, aligned reads generated by the node and received from the other nodes, thereby obtaining a sorted list of aligned reads, and
perform a variant analysis using the sorted list of aligned reads.

23. The method of claim 22, further comprising:
splitting the sorted list into N sorted regions, and
performing a multi-threaded execution of the variant analysis on the aligned reads of the N sorted regions, each thread operating on aligned reads of one of the N sorted regions.

* * * * *